United States Patent

Englert et al.

[11] Patent Number: 5,849,755
[45] Date of Patent: Dec. 15, 1998

[54] 3-AMIDOCHROMANYLSULFONYL(THIO) UREAS, PROCESSES FOR THEIR PREPARATION, THEIR USE, AND PHARMACEUTICAL PREPARATIONS COMPRISING THEM

[75] Inventors: Heinrich Christian Englert, Hofheim; Uwe Gerlach, Hattersheim; Dieter Mania, Königstein; Wolfgang Linz, Mainz; Heinz Gögelein, Frankurt; Erik Klaus, Kelkheim, all of Germany

[73] Assignee: Hoechst Aktiengesellschaft, Frankfurt am Main, Germany

[21] Appl. No.: 969,794

[22] Filed: Nov. 13, 1997

[30] Foreign Application Priority Data

Nov. 14, 1996 [DE] Germany .................. 196 47 000.5

[51] Int. Cl.$^6$ ............ C07D 311/58; C07D 405/12; A61K 31/35
[52] U.S. Cl. ........... 514/309; 514/183; 514/212; 514/320; 514/414; 514/422; 514/456; 540/463; 540/524; 546/141; 546/196; 548/454; 548/525; 549/404
[58] Field of Search ................ 540/463, 524; 546/141, 196; 548/454, 525; 549/404; 514/183, 212, 309, 320, 414, 422, 456

[56] References Cited

U.S. PATENT DOCUMENTS 5,574,069 11/1996 Englert et al. .................. 514/586
5,652,268 7/1997 Englert et al. .................. 514/584

FOREIGN PATENT DOCUMENTS

| A-0325964 | 8/1989 | European Pat. Off. |
| 0 587 180 | 3/1994 | European Pat. Off. |
| A-0612724 | 8/1994 | European Pat. Off. |
| 0727 416 | 8/1996 | European Pat. Off. |
| 0779 288 | 6/1997 | European Pat. Off. |
| A-0799288 | 6/1997 | European Pat. Off. |

OTHER PUBLICATIONS

P. Smits et al.; "Cardiovascular Effects of Sulphonylurea Derivatives Implications for the Treatment of NIDDM", Diabetologia, vol. 38, pp. 116–121, Jan. 1, 1995.

*Primary Examiner*—Zinna Northington Davis
*Attorney, Agent, or Firm*—Finnegan, Henderson, Farabow, Garrett & Dunner, L.L.P.

[57] ABSTRACT

3-amidochromanylsulfonyl(thio)ureas of the formula (I):

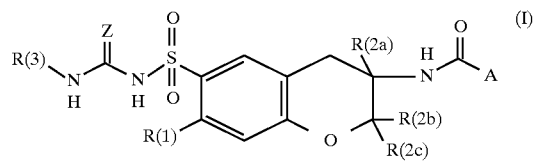

which are valuable pharmaceutically active compounds for the treatment of disturbances of the cardiovascular system, in particular for the treatment of arrhythmias, for preventing sudden cardiac death or for influencing a reduced contractility of the heart, and processes for their preparation, their use and pharmaceutical preparations comprising them.

22 Claims, No Drawings

3-AMIDOCHROMANYLSULFONYL(THIO) UREAS, PROCESSES FOR THEIR PREPARATION, THEIR USE, AND PHARMACEUTICAL PREPARATIONS COMPRISING THEM

BACKGROUND OF THE INVENTION

The present invention relates to 3-amidochromanylsulfonyl(thio)ureas of the formula I:

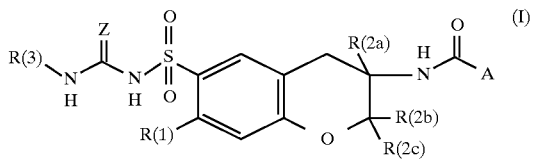

which are valuable pharmaceutically active compounds for the treatment of disturbances of the cardiovascular system, in particular for the treatment of arrhythmias, for preventing sudden cardiac death or for influencing a reduced contractility of the heart, and to processes for their preparation, their use, and pharmaceutical preparations comprising them.

For certain benzenesulfonylureas, a hypoglycemic action has been described. The prototype of such hypoglycemic sulfonylureas is glibenclamide which is used therapeutically as an agent for the treatment of diabetes mellitus and which in research serves as a highly regarded tool for investigating so-called ATP-sensitive potassium channels. In addition to its hypoglycemic action, glibenclamide also has other actions which it has not yet been possible to employ therapeutically, but which are all attributed to the blocking of precisely these ATP-sensitive potassium channels. These actions include, in particular, an antifibrillatory action on the heart. However, a simultaneous lowering of blood sugar would be undesirable or even dangerous during treatment of ventricular fibrillation or its preliminary stages, since it may deteriorate the condition of the patient further. EP-A-612 724 discloses benzenesulfonylureas which have actions on the cardiovascular system. German patent application 19546736.1 and EP-A-779 288 describe chromanylsulfonyl(thio)ureas which have an action on the cardiovascular system and in which an amido group is linked with the 4-position of the chroman system via a methylene or ethylene group. However, the properties of these compounds are still not satisfactory in various respects, and there continues to be a need for compounds with a favorable property profile which are suitable in particular for the treatment of arrhythmic disturbances of the heart and their consequences.

EP-A-325 964 describes chroman compounds as $\alpha_2$-adrenergic antagonists having an action against depression, metabolic disturbances, glaucoma, migraines and high blood pressure. However, no compounds with substitution by sulfonylurea or sulfonylthiourea groupings are described and neither are such compounds suggested.

SUMMARY OF THE INVENTION

Surprisingly, the inventors have now found that chromanylsulfonyl(thio)ureas of the formula I having an amido group in the 3-position of the chroman system have a pronounced action on the cardiovascular system. The present invention thus relates to compounds of the formula I

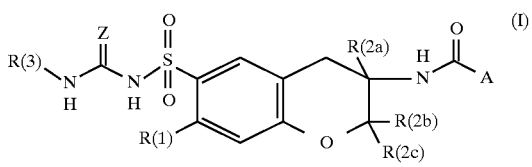

in which

R(1) is hydrogen, alkyl having 1, 2, 3 or 4 carbon atoms, alkoxy having 1, 2, 3 or 4 carbon atoms, alkoxyalkoxy having 1, 2, 3 or 4 carbon atoms independently of one another in each of the two alkoxy units, alkylmercapto having 1, 2, 3 or 4 carbon atoms, fluorine, chlorine, bromine, iodine or trifluoromethyl;

R(2a), R(2b) and R(2c), which are identical or different, are hydrogen or alkyl having 1 or 2 carbon atoms;

R(3) is hydrogen or alkyl having 1, 2, 3 or 4 carbon atoms;

Z is sulfur or oxygen;

A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

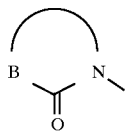

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system of the formulae

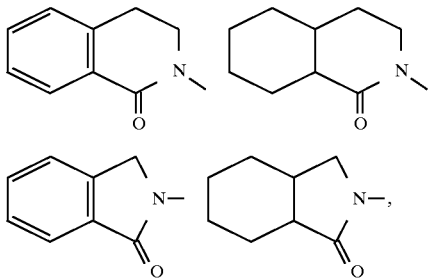

in all their stereoisomeric forms and mixtures thereof in any ratio;

and their physiologically acceptable salts.

Unless stated otherwise, the term alkyl means straight-chain or branched saturated hydrocarbon radicals. This also applies to alkyl radicals which are contained in an alkoxy radical, that is in the radical alkyl-O—, or which are contained in an alkoxyalkoxy radial, that is in the radical alkyl-O-alkyl-O—, or which are contained in an alkylmercapto radical, that is in the radical alkyl-S—. Examples of alkyl radicals are methyl, ethyl, n-propyl, isopropyl, n-butyl, isobutyl, sec-butyl and tert-butyl. Examples of alkoxy radicals are methoxy, ethoxy, n-propoxy, isopropoxy, n-butoxy, isobutoxy, sec-butoxy and tert-butoxy. Examples of alkoxyalkoxy are methoxymethoxy, ethoxymethoxy, n-butoxymethoxy, 2-methoxyethoxy, 2-ethoxyethoxy, 2-isopropoxyethoxy, 2-(n-propoxy)ethoxy, 2-(n-butoxy)ethoxy, 2-isobutoxyethoxy, 2-(tert-butoxy)ethoxy, 3-methoxypropoxy, 3-ethoxypropoxy, 2-methoxypropoxy, 2-ethoxypropoxy, 4-methoxybutoxy, 4-ethoxybutoxy and 3-methoxybutoxy.

Examples of group B alkylene and alkenylene radicals are 1,3-propylene, 1,4-butylene, 1,5-pentylene, 1,6-hexylene, 1,3-prop-1-enylene, 1,3-prop-2-enylene, 1,4-but-1-enylene, 1,4-but-2-enylene, 1,4-but-3-enylene, 1,5-pent-1-enylene, 1,5-pent-2-enylene 1,5-pent-3-enylene and 1,5-pent-4-enylene.

In substituted phenyl radicals, which can be, in particular, mono-, di- or trisubstituted, the substituents can be in any desired position, in the case of monosubstitution, for example, in the ortho-, meta- or para-position, in the case of disubstitution, for example, in the 2,3-, 2,4-, 2,5-, 2,6-, 3,4-, or 3,5-position, and in the case of trisubstitution, for example, in the 2,3,4-, 2,3,5-, 2,3,6-, 2,4,5-, 2,4,6- or 3,4,5-position.

Unless stated otherwise, halogen is fluorine, chlorine, bromine and iodine, and preferably fluorine and chlorine.

Compounds of the formula I can have one or more centers of chirality, for example on the carbon atoms 2 or 3 of the chroman system if they are appropriately substituted, and can exist in stereoisomeric forms. Chiral centers which are present can have the R or S configuration, independently of one another. The invention includes all the possible stereoisomers, for example enantiomers or diastereomers, and mixtures of two or more stereoisomers in any desired ratios. The invention relates to enantiomers, for example, in the form of the pure enantiomers, both as levo- and as dextrorotatory antipodes, in the form of racemates and in the form of mixtures of the two enantiomers in any desired ratios.

The compounds of the formula I according to the invention contain mobile hydrogen atoms and can exist in various tautomeric forms. The present invention also relates to all these tautomers.

Physiologically tolerated salts of the compounds of the formula I are, in particular, pharmaceutically usable salts or non-toxic salts. Such salts can be prepared, for example, from compounds of the formula I having acidic hydrogen atoms and non-toxic inorganic or organic bases, for example suitable alkali metal or alkaline earth metal compounds such as sodium hydroxide or potassium hydroxide, or ammonia or organic amino compounds or ammonium hydroxides. Reactions of compounds of the formula I with bases for the preparation of the salts are in general carried out in a solvent or diluent in accordance with customary procedures. Physiologically acceptable salts of the compounds of the formula I in which alkali metal and alkaline earth metal ions such as sodium, potassium, rubidium, magnesium and calcium ions, the unsubstituted ammonium ion or ammonium ions having one or more organic radicals are present as cations, and addition products of compounds of the formula I and amino acids, in particular basic amino acids such as, for example, lysine or arginine, are preferred. Salt formation on the urea group nitrogen atom substituted by the sulfonyl group leads to compounds of the formula II

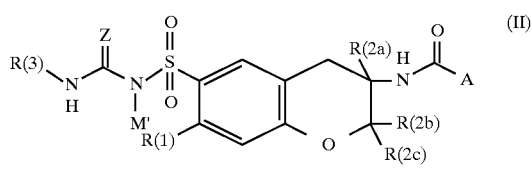

in which R(1), R(2a), R(2b), R(2c), R(3), A and Z have the meanings given above and the cation M' is, for example, an alkali metal ion or one equivalent of an alkaline earth metal ion, for example the sodium, potassium, rubidium, magnesium or calcium ion, the unsubstituted ammonium ion or an ammonium ion having one or more organic radicals, for example the cation obtained from an amino acid, in particular a basic amino acid such as, for example, lysine or arginine, by protonation.

DETAILED DESCRIPTION OF THE PREFERRED EMBODIMENTS

R(1) is preferably hydrogen, alkyl having 1 or 2 carbon atoms, alkoxy having 1, 2, 3 or 4 carbon atoms, alkylmercapto having 1, 2, 3 or 4 carbon atoms, fluorine, chlorine, bromine, iodine or trifluoromethyl; more preferably hydrogen, alkyl having 1 or 2 carbon atoms, alkoxy having 1 or 2 carbon atoms, alkylmercapto having 1 or 2 carbon atoms, fluorine, chlorine, bromine, iodine or trifluoromethyl; and particularly preferably hydrogen, alkyl having 1 or 2 carbon atoms, alkoxy having 1 or 2 carbon atoms or alkylmercapto having 1 or 2 carbon atoms.

R(2a) is preferably hydrogen. R(2b) and R(2c) are preferably, independently of one another, hydrogen or methyl, and are more preferably hydrogen.

R(3) is preferably hydrogen, methyl or ethyl.

Preferred compounds of the formula I are those in which:

R(1) is hydrogen, alkyl having 1 or 2 carbon atoms, alkoxy having 1, 2, 3 or 4 carbon atoms, alkylmercapto having 1, 2, 3 or 4 carbon atoms, fluorine, chlorine, bromine, iodine or trifluoromethyl;

R(2a), R(2b) and R(2c), which are identical or different, are hydrogen or alkyl having 1 or 2 carbon atoms;

R(3) is hydrogen or alkyl having 1, 2, 3 or 4 carbon atoms;

Z is sulfur or oxygen;

A is phenyl which is unsubstituted or substituted by up to three identical or different substituents selected from the group consisting of halogen, alkyl having 1 or 2 carbon atoms and alkoxy having 1 or 2 carbon atoms, or A is the radial of a saturated or unsaturated lactam of the formula

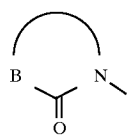

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system of the formulae

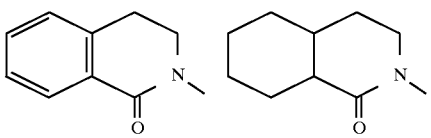

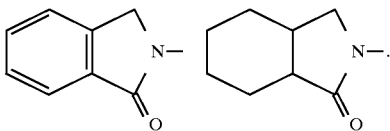

More preferred compounds of the formula I are those in which:

R(1) is hydrogen, alkyl having 1 or 2 carbon atoms, alkoxy having 1 or 2 carbon atoms, alkylmercapto having 1 or 2 carbon atoms, fluorine, chlorine, bromine, iodine or trifluoromethyl;
R(2a) is hydrogen and R(2b) and R(2c) are hydrogen or methyl;
R(3) is hydrogen or alkyl having 1, 2, 3 or 4 carbon atoms;
Z is sulfur or oxygen;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

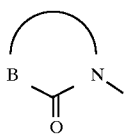

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system of the formulae

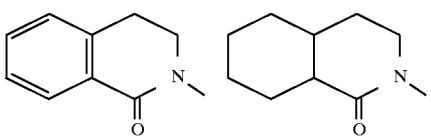

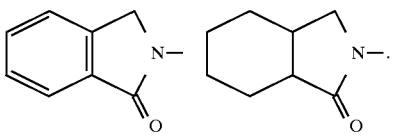

A series of particularly preferred compounds is formed by those compounds of the formula I in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen or alkyl having 1, 2, 3 or 4 carbon atoms;
Z is sulfur;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

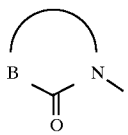

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system of the formulae

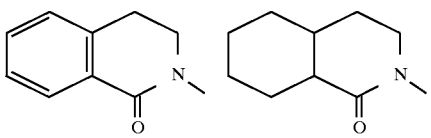

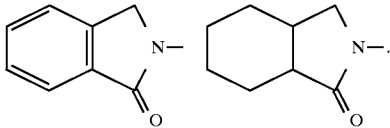

In this series, preferred compounds of the formula I are those in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is sulfur;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

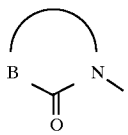

in which B is alkenylene or alkylene having 3, 4, 5 or 6 carbon atoms, which radical is unsubstituted or substituted by up to three identical or different alkyl groups having 1, 2, 3 or 4 carbon atoms.

In this series, more preferred compounds of the formula I are those in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is sulfur;
A is phenyl which is unsubstituted or substituted by up to three identical or different substituents selected from the group consisting of halogen, alkyl having 1 or 2 carbon atoms and alkoxy having 1 or 2 carbon atoms.

Another series of particularly preferred compounds is formed by those compounds of the formula I in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen or alkyl having 1, 2, 3 or 4 carbon atoms;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

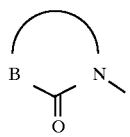

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system of the formulae

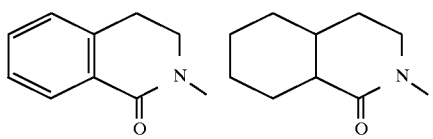

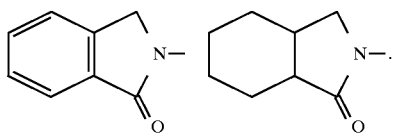

In this further series, preferred compounds of the formula I are those in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

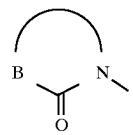

in which B is alkenylene or alkylene having 3, 4, 5 or 6 carbon atoms, which radical is unsubstituted or substituted by up to three identical or different alkyl groups having 1, 2, 3 or 4 carbon atoms.

In this further series, more preferred compounds of the formula I are those in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms.

Also with respect to all preferred compounds of the formula I, the present invention includes all their stereoisomeric forms and mixtures thereof in any ratio, and to their physiologically acceptable salts.

The invention furthermore relates to processes for the preparation of the compounds of the formula I which comprise the reaction steps described below.

(a) 3-Amidochromanylsulfonyl(thio)ureas of the formula I in which R(3) has a meaning other than hydrogen can be prepared by reacting chromanylsulfonamides of the formula III

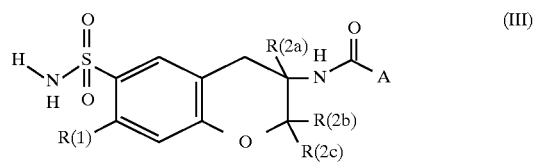

or salts thereof of the formula IV

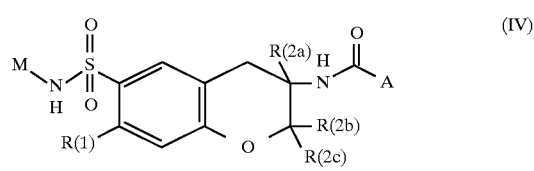

with R(3)-substituted isocyanates of the formula V or R(3)-substituted isothiocyanates of the formula VI $$R(3)-N=C=O \qquad (V)$$

R(3)—N=C=S (VI)

to give substituted chromanylsulfonylureas of the formula Ia

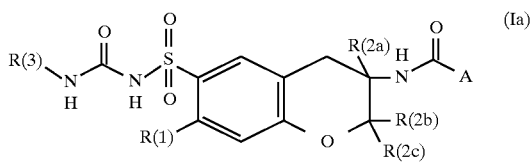

or substituted chromanylsulfonylthioureas of the formula Ib

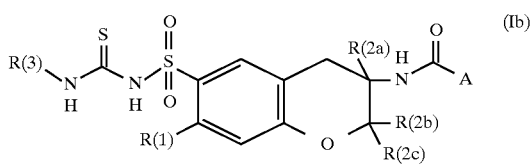

The radicals R(1), R(2a), R(2b), R(2c) and A in the formulae Ia, Ib, III and IV have the abovementioned meanings here, R(3) here in the formulae Ia and Ib and in the formulae V and VI is alkyl having 1, 2, 3 or 4 carbon atoms. Possible cations M in the salts of the formula IV are, for example, alkali metal or alkaline earth metal ions, for example the sodium or the potassium ion, or suitable ammonium ions which do not react with the reaction partners in an undesirable manner, in particular, for example, tetraalkylammonium ions or trialkylbenzylammonium ions.

As an equivalent to the R(3)-substituted isocyanates of the formula V, R(3)-substituted carbamic acid esters, R(3)-substituted carbamic acid halides or R(3)-substituted ureas can be employed.

(b) Chromanylsulfonylureas of the formula Ia can be prepared from chromanylsulfonamides of the formula III or salts thereof of the formula IV with R(3)-substituted trichloroacetamides of the formula VII

in which R(3) is alkyl having 1, 2, 3 or 4 carbon atoms, in the presence of a base in an inert solvent at temperatures of 25° to 150° C., in accordance with Synthesis 1987, 734–735, the disclosure of which is incorporated herein by reference.

Suitable bases for use in accordance with the claimed invention are, for example, alkali metal or alkaline earth metal hydroxides, hydrides, amides or alcoholates such as sodium hydroxide, potassium hydroxide, calcium hydroxide, sodium hydride, potassium hydride, calcium hydride, sodium amide, potassium amide, sodium methylate, sodium ethylate, potassium methylate or potassium ethylate. Suitable inert solvents are ethers such as tetrahydrofuran (THF), dioxane, ethylene glycol dimethyl ether or diglyme, ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoric acid triamide, sulfoxides such as dimethyl sulfoxide (DMSO), and sulfones such as sulfolane and hydrocarbons such as benzene, toluene and xylene. Furthermore, mixtures of these solvents with one another are also suitable.

(c) Chromanylsulfonyl(thio)ureas of the formula I in which R(3) is hydrogen can be prepared by reaction of chromanylsulfonamides of the formula III or of salts thereof of the formula IV with trialkylsilyl iso(thio)cyanates, for example trimethylsilyl iso(thio)cyanate, or with silicon tetraiso(thio)cyanate and cleavage (for example hydrolysis) of the primary silicon-substituted chromanylsulfonyl(thio)ureas. Using trialkylsilyl isocyanates or silicon tetraisocyanate, compounds of the formula Ic

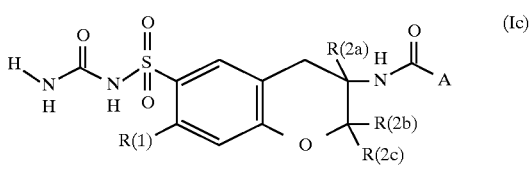

are thus obtained, and using trialkylsilyl isothiocyanates or silicon tetraisothiocyanate, compounds of the formula Id

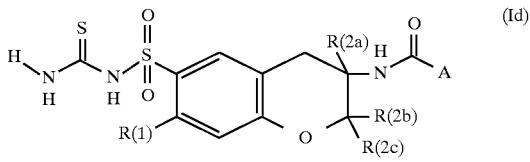

are thus obtained; the radicals R(1), R(2a), R(2b), R(2c) and A in the formulae Ic and Id having the abovementioned meanings.

It is furthermore possible to convert chromanylsulfonamides of the formula III or salts thereof of the formula IV into chromanylsulfonylureas of the formula Ic by reaction with halocyanogens and hydrolysis of the N-cyanosulfonamides primarily formed with mineral acids at temperatures of 0° to 100° C.

Chromanylsulfonylthioureas of the formula Id can also be obtained by reaction of chromanylsulfonamides of the formula III or salts thereof of the formula IV with benzoyl isothiocyanate and reaction of the intermediate benzoyl-substituted chromanylsulfonylthioureas with an aqueous mineral acid. Similar processes are described in J. Med. Chem. 35 (1992), 1137–1144, the disclosure of which is incorporated herein by reference. Another variant for the preparation of the compounds of the formula Id comprises reacting the abovementioned N-cyanosulfonamides with hydrogen sulfide.

(d) Chromanylsulfonylureas of the formula I in which Z is oxygen can be prepared from chromanylsulfonyl halides, for example of the formula VIII

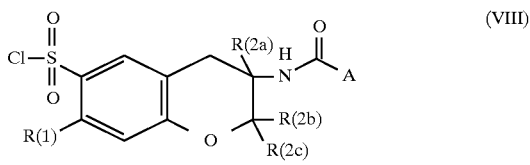

in which R(1), R(2a), R(2b), R(2c) and A have the abovementioned meanings, with R(3)-substituted ureas or R(3)-substituted bis(trialkylsilyl)ureas. Furthermore, sulfonic acid chlorides of the formula VIII can be reacted with parabanic acid to give chromanylsulfonylparabanic acids, hydrolysis of which with mineral acids gives corresponding chromanylsulfonylureas of the formula I in which Z is oxygen.

(e) Chromanylsulfonyl(thio)ureas of the formula I can also be prepared by reaction of amines of the formula R(3)-NH$_2$, in which R(3) has the abovementioned meanings, with chromanylsulfonyl isocyanates of the formula IX

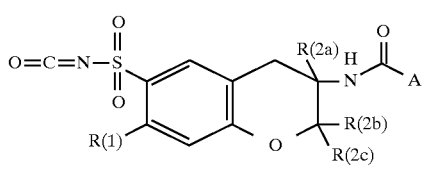

or chromanylsulfonyl isothiocyanates of the formula X

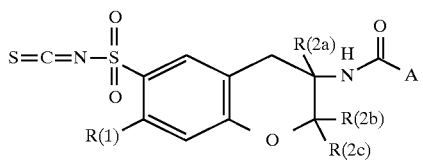

in which R(1), R(2a), R(2b), R(2c) and A in the formulae IX and X have the abovementioned meanings. As with the iso(thio)cyanates of the formulae IX and X, an amine of the formula R(3)-NH$_2$ can be reacted with a chromanylsulfonylcarbamic acid ester or -carbamic acid halide or a chromanylsulfonylurea of the formula Ia in which R(3) here is hydrogen, to give a compound of the formula I in which Z is oxygen. Similarly, an amine of the formula R(3)-NH$_2$ can be reacted with a chromanylsulfonylcarbamic acid thioester or -carbamic acid thiohalide to give a compound of the formula I in which Z is sulfur.

The sulfonyl isocyanates of the formula IX can be obtained from the sulfamoylchromans of the formula III by customary methods, for example with phosgene. The preparation of the sulfonyl isothiocyanates of the formula X can be carried out by reaction of a corresponding sulfonic acid amide of the formula III with an alkali metal hydroxide and carbon disulfide in an organic solvent such as DMF, DMSO or N-methylpyrrolidone. The resulting di-alkali metal salt of the sulfonyldithiocarbamic acid can be reacted with a slight excess of phosgene or of a phosgene substitute such as triphosgene, with a chloroformic acid ester (2 equivalents) or with thionyl chloride in an inert solvent. The resulting solution of the sulfonyl isothiocyanate can be reacted directly with the corresponding amines or ammonia.

(f) Substituted chromanylsulfonylureas of the formula I in which Z is oxygen can be prepared by a conversion reaction from chromanylsulfonylthioureas of the formula I in which Z is sulfur. The desulfurization, that is the replacement of the sulfur atom in the correspondingly substituted chromanylsulfonylthiourea by an oxygen atom, can be carried out, for example, with the aid of oxides or salts of heavy metals, or by using oxidizing agents such as hydrogen peroxide, sodium peroxide or nitrous acid. A thiourea can also be desulfurized by treatment with chlorinating agents such as phosgene or phosphorus pentachloride. Chloroformic acid amidines or carbodiimides are obtained as intermediate compounds and can be converted into the corresponding substituted chromanylsulfonylureas, for example, by hydrolysis or by adding water.

(g) Correspondingly substituted chromanylsulfenyl- or sulfinylureas can be oxidized to chromanylsulfonylureas of the formula I in which Z is oxygen with an oxidizing agent such as hydrogen peroxide, sodium peroxide or nitrous acid.

The starting compounds for the synthesis processes mentioned for the chromanylsulfonyl(thio)ureas of the formula I can be prepared by methods known per se such as are described in the literature, for example, in the standard works such as Houben-Weyl, Methoden der Organischen Chemie [Methods of organic chemistry], Thieme Verlag, Stuttgart; Organic Reactions, John Wiley & Sons, Inc., New York, the disclosure of which is incorporated herein by reference, and in the abovementioned patent applications, and under reaction conditions which are known and suitable for the reactions mentioned. Variants which are known per se but which are not mentioned in more detail here can also be utilized for these reactions. If desired, the starting substances can also be formed in situ, so that they are not isolated from the reaction mixture but are further reacted immediately.

3-Amidochromans of the formula XVI can be prepared, for example, in accordance with the synthesis process shown in Equation I, in which the substituents have the meanings given above or explained below.

Equation I

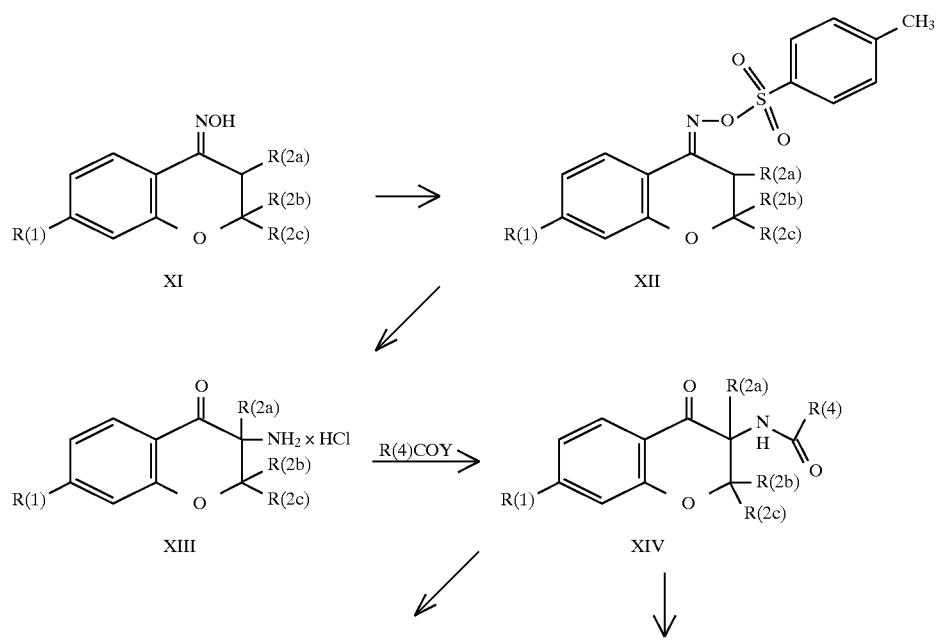

-continued
Equation I

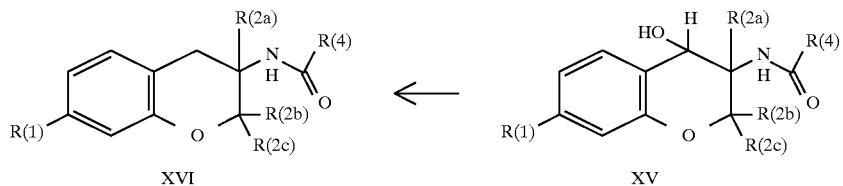

XVI                                    XV

R(4) is phenyl which is unsubstituted or substituted by up to three identical or different substituents selected from the group consisting of halogen, alkyl having 1 or 2 carbon atoms and alkoxy having 1 or 2 carbon atoms, or alkyl having 1 to 4 carbon atoms or trihalogenomethyl.

The oximes of the formula XI known from the literature, which are described, for example, in Heterocycles 38 (1994), 305–318, can be reacted with sulfonic acid chlorides, for example, p-toluenesulfonyl chloride, with the addition of tertiary bases such as, for example, pyridine or a trialkylamine, in the presence or absence of an inert solvent at temperatures of 0° to 100° C., preferably 0° to 10° C., to give oxime sulfonates, for example, to give the oxime tosylates of the formula XII. Suitable inert solvents here are, for example, ethers such as tetrahydrofuran, dioxane or glycol ether, ketones such as acetone or butanone, nitriles such as acetonitrile, amides such as dimethylformamide or N-methylpyrrolidone, hexamethylphosphoric acid triamide, sulfoxides such as DMSO, chlorinated hydrocarbons such as methylene chloride, chloroform, trichloroethylene, 1,2-dichloroethane or carbon tetrachloride, and hydrocarbons such as benzene, toluene or xylenes. Furthermore, mixtures of these solvents with one another are also suitable.

The oxime sulfonates, for example of the formula XII, can be rearranged into amino-ketones, i.e. into the 3-amino-4-chromanones, by the action of bases in a solvent. These products are in general isolated in the form of acid addition salts, for example, in the form of the hydrochlorides of the formula XIII (J. Med. Chem. 12 (1969), 277). Suitable bases for this rearrangement are, for example, the alkali metal salts of alcohols such as, for example, sodium methylate, sodium ethylate, sodium isopropylate, potassium methylate, potassium ethylate or potassium tert-butylate, and also tertiary amine bases such as pyridine or trialkylamines. Possible solvents are, for example, alcohols such as methanol, ethanol, isopropanol and tert-butanol, ethers such as tetrahydrofuran and dioxane, and hydrocarbons such as benzene, toluene and xylene. The rearrangement is in general carried out at temperatures from 10° to 100° C., preferably at 20° to 60° C.

The amino-ketones can, after conversion of the acid addition salts, i.e., for example, of the hydrochlorides of the formula XIII, with bases into the free amines be acylated to give the amides of the formula XIV, in which R(4) can be the phenyl radical described in the abovementioned definition of A, it being possible for the group R(4)-C(=O) to remain then in the molecule, or in which the group R(4)-C(=O) has the function of a protective group which is split off again in the subsequent course of the synthesis.

In the latter case R(4) is, for example, alkyl having 1 to 4 carbon atoms or trihalogenomethyl, for example trifluoromethyl. Suitable acylating agents here for the amino groups are, for example, the alkyl esters, the halides such as, for example, chlorides or bromides, or the anhydrides of carboxylic acids. The acylation can be carried out in particular with compounds of the formula R(4)-C(=O)—Y, in which, as shown in Equation II, the radical R(4) is, for example, an alkyl radical having 1 to 4 carbon atoms or a trihalogenomethyl radical, or is phenyl which is unsubstituted or substituted by up to three identical or different substituents selected from the group consisting of halogen, alkyl having 1 or 2 carbon atoms and alkoxy having 1 or 2 carbon atoms, and Y is a leaving group such as, for example, halogen, ($C_1$–$C_4$)-alkoxy, trihalogenoacetoxy or ($C_1$–$C_4$)-alkylcarbonyloxy.

The syntheses of the compounds of the formula XIV can be carried out with the addition of tertiary bases such as, for example, pyridine or trialkylamines, and in the presence or absence of an inert solvent, it also being possible for a catalyst such as, for example, dimethylaminopyridine, to be present. The reaction is in general carried out at temperatures from about 0° to 160° C., preferably from 20° to 100° C. Suitable inert solvents are, for example, ethers such as tetrahydrofuran, dioxane, glycol ethers such as ethylene glycol monomethyl or ethylene glycol monoethyl ether (methylglycol or ethylglycol), ethylene glycol dimethyl ether or diglyme, ketones such as acetone or butanone, nitriles such as acetonitrile, amides such as dimethylformamide or N-methylpyrrolidone, hexamethylphosphoric acid triamide, sulfoxides such as DMSO, chlorinated hydrocarbons such as methylene chloride, chloroform, trichloroethylene, 1,2-dichloroethane or carbon tetrachloride, and hydrocarbons such as benzene, toluene or xylenes. Furthermore, mixtures of these solvents with one another are also suitable.

The chromanones of the formula XIV can be reduced to the corresponding chromanols of the formula XV by methods known per se, for example, with alkali metal borohydrides such as sodium or potassium borohydride, in alcohols such as methanol or ethanol (Bull. Soc. Chim. Fr. 1972, 3183).

The chromanones of the formula XIV, and also the chromanols of the formula XV, can be reduced to the amidochromanes of the formula XVI, for example by catalytic hydrogenation. Suitable catalysts for this hydrogenation are, for example, metals such as Pt, Pd, Rh, Ru and Raney nickel, it being possible for the first four mentioned also to be in the form of metal oxides. Pd, Pt and Raney nickel are preferred. Suitable solvents for the hydrogenation are, for example, alcohols such as methanol, ethanol or propanol, ethers such as dioxane or tetrahydrofuran, or acids, acetic acid being preferred. To accelerate the reaction, a catalytic amount of a strong acid such as concentrated sulfuric acid, hydrochloric acid, perchloric acid or trifluoroacetic acid, can be added during the hydrogenation. The hydrogenation is in general carried out at 10° to 50° C., preferably at 15° to 30° C., and under a hydrogen pressure of 0 to 100 atmospheres gauge, preferably under 0 to 5 atmospheres gauge (i.e. under an hydrogen excess pressure of 0 to 100 atmospheres, preferably 0 to 5 atmospheres) (J. Med. Chem, 15 (1972), 863–865). If acetic acid is used as the solvent, the yields can be increased by addition of anhydrides of ($C_1$–$C_4$)-alkylcarboxylic acids such as, for example, acetic anhydride. The chromanols of the formula XV can also be converted into the amidochromans of the formula XVI by further reduction methods such as are described, for example, in Larock, Comprehensive Organic Transformations, VCH, 1989, pages 27–28.

The following steps in the synthesis of the compounds of the formula I are shown in Equation II.

sodium hydroxide, potassium hydroxide, calcium hydroxide, sodium methylate, sodium ethylate, potassium methylate and potassium ethylate.

The amines of the formula XVII have one or two chiral centers on the ring carbon atoms. If they are present as mixtures of stereoisomeric forms, for example as racemates, and if stereochemically uniform compounds of the formula I are to be prepared, separation of the stereoisomers can be carried out, for example, at the stage of the amines of the

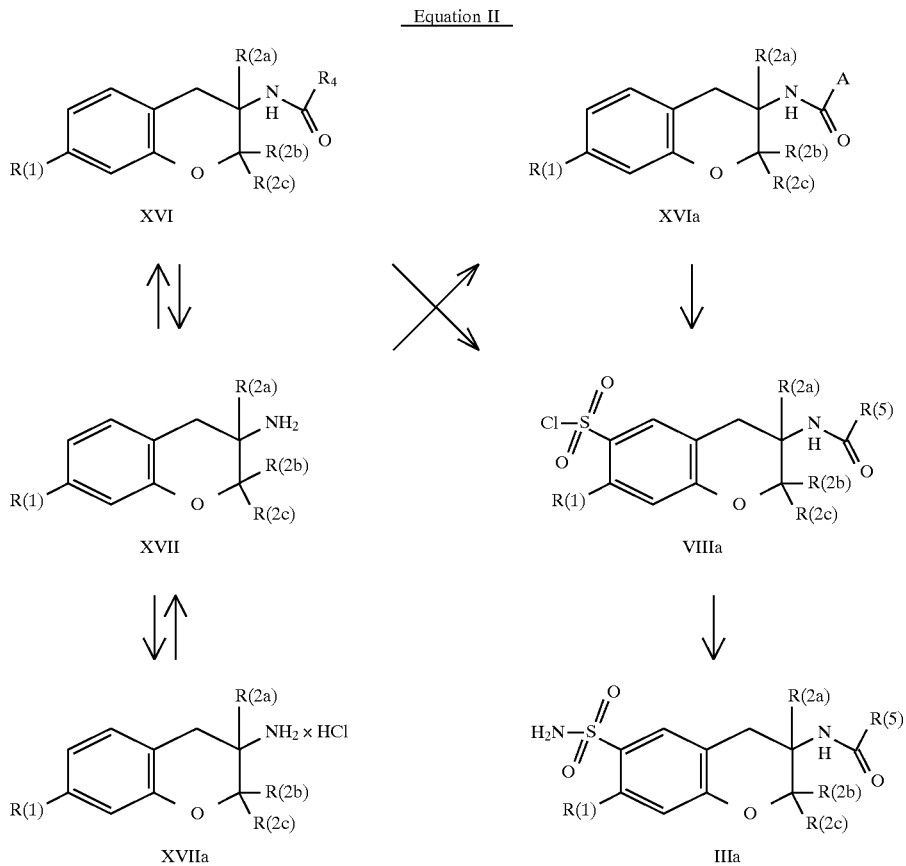

Equation II

R(4) is phenyl which is unsubstituted or substituted by up to three identical or different substituents selected from the group consisting of halogen, alkyl having 1 or 2 carbon atoms and alkoxy having 1 or 2 carbon atoms, or alkyl having 1 to 4 carbon atoms or trihalogenomethyl, and
R(5) has all the abovementioned meanings of A or is alkyl having 1 to 4 carbon atoms or trihalogenomethyl If the acyl group R(4)-C(=O) in the compounds of the formula XVI functions as a protective group, it can be split off again by acids or bases, the aminochromans of the formula XVII being formed. By cleavage with acids, for example with aqueous acids or with acids in inert organic solvents, the associated acid addition salt, for example the hydrochloride of the formula XVIIa, can be formed. Acids which are suitable for the cleavage are, for example, sulfuric acid, hydrohalic acids such as hydrochloric acid or hydrobromic acid, phosphoric acids such as orthophosphoric acid or polyphosphoric acid, or other customary acids with which amides can be cleaved, for example organic carboxylic, sulfonic or sulfuric acids such as, for example, acetic acid, salicylic acid, methane- or ethanesulfonic acid, benzenesulfonic acid, p-toluenesulfonic acid or laurylsulfuric acid. The cleavage of the acylated amine of the formula XVI with bases can likewise be carried out in aqueous or inert organic solvents. Suitable bases are, for example, alkali metal or alkaline earth metal hydroxides or alcoholates such as formula XVII. If the amines of the formula XVII have two or more chiral centers, they can be obtained in the synthesis as mixtures of racemates, from which individual racemates can be isolated in the pure form, for example by recrystallization from inert solvents. Resulting racemates can, if desired, be separated mechanically or chemically into their enantiomers by methods known per se. Thus, diastereomers can be formed from the racemate by reaction with an optically active separating agent. Suitable separating agents for basic compounds are, for example, optically active acids such as the R or R,R and S or S,S forms of tartaric acid, dibenzoyltartaric acid, diacetyltartaric acid, camphorsulfonic acid, mandelic acid, maleic acid and lactic acid. The various forms of the diastereomers can be separated in a manner known per se, for example by fractional crystallization, and the enantiomers can be liberated from the diastereomers in a manner known per se. Separations of enantiomers are furthermore achieved by chromatography on optically active support materials. A particularly simple process for the preparation of optically uniform compounds, with appropriate substitution, comprises, for example, resolving the amines of the formula XVII into the enantiomers by crystallization or recrystallization of the salts with optically active acids such as, for example, (+)- or (−)-mandelic acid and converting these enantiomers into the end compounds of the formula I, which are then in turn enantiomerically pure. To prepare stereochemically uniform compounds of the formula I, for example pure enantiomers, however, separations can also be carried out by the methods mentioned or other customary methods at other stages of the synthesis.

The compounds of the formula XVII, i.e., including stereochemically uniform forms, can be acylated to give the amides of the formula XVIa or XVI. Suitable acylating agents here for introducing the group A-C(=O), in which A is phenyl which is unsubstituted or substituted by up to three identical or different substituents selected from the group consisting of halogen, alkyl having 1 or 2 carbon atoms and alkoxy having 1 or 2 carbon atoms, and which can remain in the molecule, are, for example, the alkyl esters, the halides, such as, for example, chlorides or bromides, or the anhydrides of benzoic acids. In particular, the acylation can be carried out with compounds of the formula A-C(=O)—Y, in which A is phenyl which is unsubstituted or substituted by up to three identical or different substituents selected from the group consisting of halogen, alkyl having 1 or 2 carbon atoms and alkoxy having 1 or 2 carbon atoms, and Y is a leaving group such as, for example, halogen, $(C_1–C_4)$-alkoxy, trihalogenoacetoxy or $(C_1–C_4)$-alkylcarbonyloxy. This acylation can in turn be carried out with the addition of tertiary bases such as, for example, pyridine or trialkylamines, and in the presence or absence of an inert solvent; it also being possible for a catalyst such as, for example, dimethylaminopyridine, to be present. The reaction is in general carried out at temperatures of about 0° to 160° C., preferably 20° to 100° C. Suitable inert solvents are, for example, ethers such as tetrahydrofuran, dioxane, glycol ethers such as ethylene glycol monomethyl or ethylene glycol monoethyl ether (methyl glycol or ethyl glycol), ethylene glycol dimethyl ether or diglyme, ketones such as acetone or butanone, nitrites such as acetonitrile, amides such as dimethylformamide or N-methylpyrrolidone, hexamethylphosphoric acid triamide, sulfoxides such as DMSO, chlorinated hydrocarbons such as methylene chloride, chloroform, trichloroethylene, 1,2-dichloroethane or carbon tetrachloride, or hydrocarbons such as benzene, toluene or xylenes. Mixtures of these solvents with one another are furthermore also suitable.

The preparation of those compounds of the formula XVIa in which A is a radical of the formula

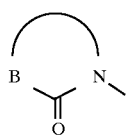

or a radical of the formulae

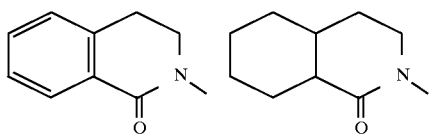

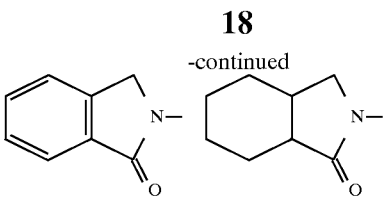

can be carried out, for example, by the following routes. In one route, the amine of the formula XVII is first converted into an isocyanate of the formula XVIII

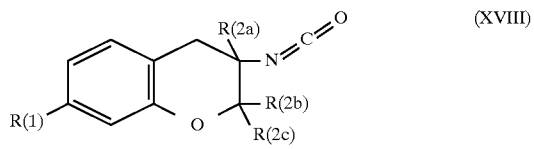

in which R(1), R(2a), R(2b) and R(2c) have the abovementioned meanings, by reaction with carbonic acid halides such as phosgene or triphosgene, in the presence of tertiary alkylamines or pyridine and inert solvents in a manner known per se. Suitable inert solvents are, for example, ethers such as tetrahydrofuran, dioxane, ethylene glycol dimethyl ether or diglyme, ketones such as acetone or butanone, nitriles such as acetonitrile, nitro compounds such as nitromethane, esters such as ethyl acetate, amides such as dimethylformamide or N-methylpyrrolidone, hexamethylphosphoric acid triamide, sulfoxides such as DMSO, sulfones such as sulfolane, or hydrocarbons such as benzene, toluene or xylenes. Furthermore, mixtures of these solvents with one another are also suitable. In another route, the amines of the formula XVII are first converted in a manner known per se into reactive carbonic acid derivatives, for example into carbonic acid esters (urethanes) such as can be synthesized from chloroformic acid alkyl esters and amines of the formula XVII in the presence of suitable tertiary alkylamines or pyridines. Furthermore, N,N'-carbonyldiimidazole and analogous reactive derivatives can also be employed as isocyanate equivalents (H. A. Staab, Synthesen mit heterocyclischen Amiden (Azoliden) [Syntheses with heterocyclic amides (azolides)], Angewandte Chemie 74 (1962), 407–423).

The isocyanates of the formula XVIII or the urethanes or the intermediate compounds obtained from amines of the formula XVII and, for example, N,N'-carbonyldiimidazole, can then be coupled with a compound of the formula

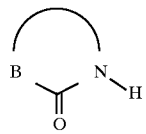

in which B has the abovementioned meaning, or a compound of the formulae

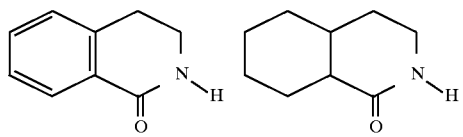

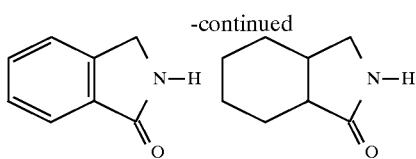

in the presence or absence of inert solvents at temperatures of 100° to 170° C. (Justus Liebigs Ann. Chem. 598 (1956), 203), and give the corresponding compounds of the formula XVIa in which A is one of the heterocyclic radicals.

The sulfonamides of the formula IIIa can be prepared from the acylated amines of the formulae XVI and XVIa under suitable reaction conditions known per se in a manner known per se (cf. Equation II). Variants which are known per se but are not mentioned here can also be utilized for this reaction. The syntheses of the sulfonamides can be brought to completion in one, two or more steps. Processes in which the acylated amines of the formula XVI or XVIa are converted into the 6-chromanylsulfonic acids or derivatives thereof, for example sulfonic acid halides of the formula VIIIa, by electrophilic reagents in the presence or absence of inert solvents at temperatures of −10° C. to 120° C., preferably 0° to 100° C., are particularly preferred. For this conversion, for example, it is possible to carry out sulfonations with sulfuric acids or oleum, halogenosulfonations with halogenosulfonic acids such as chlorosulfonic acid, reactions with sulfuryl halides in the presence of anhydrous metal halides, or reactions with thionyl halides in the presence of anhydrous metal halides with subsequent oxidations carried out in a known manner to give sulfonic acid chlorides. If sulfonic acids are the primary reaction products, these can be converted into sulfonic acid halides, for example of the formula VIIIa, by means of acid halides such as, for example, phosphorus trihalides, phosphorus pentahalides, phosphorus oxychlorides, thionyl halides or oxalyl halides, in a manner known per se, either directly or after treatment with tertiary amines such as, for example, pyridine or trialkylamines, or with alkali metal or alkaline earth metal hydroxides or with reagents which form these basic compounds in situ. The conversion of the sulfonic acid derivatives into sulfonamides of the formula IIIa is carried out in a manner known from the literature, sulfonic acid chlorides preferably being reacted with aqueous ammonia in inert solvents at temperatures of 0° to 100° C.

For synthesis of the compounds of the formula I, corresponding sulfonamides of the formula IIIa in which the group R(5)-C(=O) has the function of a protective group can also be prepared from the acylated amines of the formula XVI. As shown in Equation II, the group R(5) contained in the formulae VIIIa and IIIa can have the abovementioned meanings of A, but, in the same way as R(4), can also be, for example, alkyl having 1 to 4 carbon atoms or trihalogenomethyl. If R(5) in the formula IIIa has the meanings of A, the compounds of the formula III are present. If R(5) in the formula VIIIa has the meanings of A, the compounds of the formula VIII are present.

The protective group can be split off from the compounds of the formula IIIa which contain a protective group, after introduction of the sulfonamide group, by means of acids or bases as is explained above for splitting off the protective group from the compounds of the formula XVI. The sulfamoylchromans of the formula III can then be prepared from the sulfonamide-substituted amines thus prepared, as explained above for the introduction of the group A-C(=O) into the compounds of the formulae XIII and XVII. One or the other of the processes mentioned and their embodiments may be less suitable for the synthesis of the compounds of the formula I, or at least necessitate measures to protect reactive groups, depending on the nature of the radicals R(1), R(2a), R(2b), R(2c), R(3), A and Z. However, such relatively rarely occurring cases can easily be recognized by the skilled person, and there are no difficulties in successfully applying another of the synthesis routes described in such cases.

The compounds of the formula I influence the action potential of cells, in particular of myocardial cells. They have a normalizing action on an impaired action potential such as exists, for example, during ischemias, and are therefore suitable, for example, for the treatment and prophylaxis of disturbances of the cardiovascular system, in particular of arrhythmias and their consequences. The activity of the compounds of the formula I can be demonstrated, for example, in the model described below, in which the duration of the action potential of the papillary muscle of the guinea pig is determined.

The compounds of the formula I and their physiologically acceptable salts can therefore be used, by themselves, as mixtures with one another or in the form of pharmaceutical formulations, as medicaments in animals, preferably in mammals, and particularly preferably in humans. Mammals in which the compounds of the formula I can be used or tested are, for example, monkeys, dogs, mice, rats, rabbits, guinea pigs, cats and larger stock animals such as, for example, cattle and pigs. The present invention also relates to the compounds of the formula I and/or their physiologically acceptable salts for use as medicaments and to pharmaceutical formulations which comprise, as the active constituent, an effective dose of at least one compound of the formula I and/or of a physiologically acceptable salt thereof, in addition to customary, pharmaceutically acceptable carriers and auxiliaries. The pharmaceutical formulations can be intended for enteral or parenteral use, and usually comprise 0.5 to 90 percent by weight of the compounds of the formula I and/or their physiologically acceptable salts.

The pharmaceutical formulations according to the invention can be prepared in a manner known per se. For this, the compounds of the formula I and/or their physiologically acceptable salts can be brought into a suitable dosage form and administration form together with one or more solid or liquid carriers and/or auxiliaries and, if desired, in combination with other medicaments, for example medicaments having a cardiovascular action such as, for example, calcium antagonists or ACE inhibitors, and this form can then be used as a medicament in human or veterinary medicine.

Possible carriers are organic or inorganic substances which are suitable, for example, for enteral (for example oral) administration or for parenteral administration (for example intravenous injection of infusion) or for topical application and which do not react with the compounds of the formula I are, for example, water, vegetable oils, waxes, alcohols such as ethanol, propanediol or benzyl alcohols, glycerol, polyols, polyethylene glycols, polypropylene glycols, glycerol triacetate, gelatin, carbohydrates such as lactose or starch, stearic acid and salts thereof such as magnesium stearate, talc, lanolin or Vaseline. Drug forms such as tablets, coated tablets, capsules, suppositories, solutions, preferably oily or aqueous solutions, syrups, juices or drops, and furthermore suspensions or emulsions are used in particular for oral and rectal use. Ointments, creams, pastes, lotions, gels, sprays, foams, aerosols, solutions or powders are used in particular for topical application. Solvents which can be used for solutions are, for example, water or alcohols such as ethanol, isopropanol or 1,2-propanediol, or mixtures thereof with one another or with water. Implants, for example, are also possible further drug forms. The compounds of the formula I can also be lyophilized and the resulting lyophilizates can be used, for example, for the preparation of injection preparations. Liposomal formulations are also possible, in particular, for topical use. The pharmaceutical formulations can comprise auxiliaries such as lubricants, preservatives, disintegrating agents, thickeners, stabilizers and/or wetting agents, agents for achieving a depot effect, emulsifiers, salts (for example for influencing the osmotic pressure), buffer substances, dyestuffs, flavorings and/or aroma substances. If desired, they can also comprise one or more other active compounds and/or, for example, one or more vitamins.

The compounds of the formula I and their physiologically acceptable salts are valuable therapeutics which are suitable for use on humans or mammals not only as antiarrhythmics but also for the treatment and prophylaxis in other disturbances of the cardiovascular system, for cardiac insufficiency, ischemias or heart transplants, or for cerebral vascular diseases. They are used in particular as antiarrhythmics for the treatment of disturbances in cardiac rhythm of the most diverse origin and for preventing arrhythmia-related sudden cardiac death. Examples of arrhythmic disturbances of the heart are supraventricular dysrhythmias such as, for example, atrial tachycardias, atrial flutter or paroxysmal supraventricular dysrhythmias, or ventricular dysrhythmias such as ventricular extrasystoles, but in particular, life-threatening ventricular tachycardias or the particularly dangerous ventricular fibrillation. They are particularly suitable for those cases where arrhythmias are the consequence of a constriction of a coronary vessel such as occur, for example, with angina pectoris or during an acute cardiac infarction or as a chronic consequence of a cardiac infarction. They are therefore particularly suitable for preventing sudden cardiac death in postinfarction patients. Other syndromes where such dysrhythmias and/or sudden arrhythmia-related cardiac deaths play a role are, for example, cardiac insufficiency or cardiac hypertrophy as a consequence of a chronically increased blood pressure.

The compounds of the present invention are furthermore capable of positively influencing a reduced contractility of the heart and a weakened cardiac power. These conditions can be disease-related reductions in cardiac contractility such as, for example, in the case of cardiac insufficiency, or also acute cases such as cardiac failure under the effects of shock. Under the influence of the compounds of the formula I during a heart transplant, the heart can resume its capacity faster and more reliably after the operation has taken place. The same applies to operations on the heart which necessitate temporarily stopping cardiac activity by means of cardioplegic solutions.

The present invention also relates to the use of the compounds of the formula I and/or their physiologically acceptable salts for the treatment and prophylaxis of the syndromes mentioned and the use for the preparation of medicaments for use in these syndromes.

The dosages which are necessary, for example, for the treatment of disturbances in cardiac rhythm with the compounds of the formula I depend on whether treatment is acute or prophylactic, and depend on the particular individual case. A dose which lies in the range from about at least 0.01 mg, preferably 0.1 mg, more preferably 1 mg, to not more than 100 mg, preferably 10 mg (in each case per kg of bodyweight and day) is usually sufficient if prophylaxis is being undertaken. A dose range from 1 to 10 mg per kg and day is particularly suitable. The dose can be administered here in the form of an individual oral or parenteral dose, or can be divided into several, in particular, for example, two, three or four individual doses. If acute cases of disturbances in cardiac rhythm are being treated, for example on an intensive care ward, parenteral administration, for example by injection or infusion, may be advantageous. A preferred dose range in critical situations can then be 10 to 100 mg per kg and day, and can be administered, for example, as a continuous infusion.

The compounds of the formula I inhibit the ATP-sensitive potassium channels of cells. As well as being employed as pharmaceutically active compounds in human and veterinary medicine, the compounds of the formula I can also be employed as a scientific tool or as an aid for biochemical investigations in which such an influence on ion channels is intended, and for diagnostic purposes. The compounds of the formula I and their salts can furthermore be used as intermediate products for the preparation of other pharmaceutically active compounds.

The following compounds of the formula I, for example, can also be obtained analogously to the compounds described in the embodiment examples below:

3-(5-Chloro-2-methoxybenzamido)-6-(methylaminocarbonylaminosulfonyl)-7-ethylchroman,
3-(5-Chloro-2-methoxybenzamido)-6-(methylaminothiocarbonylaminosulfonyl)-7-ethoxychroman,
3-(5-Bromo-2-methoxybenzamido)-6-(methylaminocarbonylaminosulfonyl)-7-ethylchroman,
3-(5-Bromo-2-methoxybenzamido)-6-methylaminothiocarbonylaminosulfonyl)-7-methoxychroman,
3-(5-Chloro-2-methoxybenzamido)-6-(ethylaminocarbonylaminosulfonyl)-7-ethylchroman,
3-(5-Bromo-2-methoxybenzamido)-6-(ethylaminocarbonylaminosulfonyl)-7-ethylchroman,
3-(5-Chloro-2-methoxybenzamido)-6-(ethylaminothiocarbonylaminosulfonyl)-7-ethoxychroman,
3-(5-Bromo-2-methoxybenzamido)-6-(ethylaminothiocarbonylaminosulfonyl)-7-methoxychroman,
3-(3-Ethyl-4-methyl-2-oxo-3-pyrroline-1-carboxamido)-6-(methylaminothiocarbonylaminosulfonyl)-7-ethoxychroman,
3-(3-Ethyl-4-methyl-2-oxo-3-pyrroline-1-carboxamido)-6-(methylaminocarbonylaminosulfonyl)-7-ethoxychroman,
3-(3-Ethyl-4-methyl-2-oxo-3-pyrroline-1-carboxamido)-6-(methylaminocarbonylaminosulfonyl)-7-ethylchroman,
3-(3-Ethyl-4-methyl-2-oxo-3-pyrroline-1-carboxamido)-6-(methylaminocarbonylaminosulfonyl)-7-ethylchroman,
3-(2-Oxo-3-pyrroline-1-carboxamido)-6-(methylaminothiocarbonylaminosulfonyl)-7-ethoxychroman,
3-(2-Oxo-3-pyrroline-1-carboxamido)-6-(methylaminocarbonylaminosulfonyl)-7-ethoxychroman,
3-(2-Oxo-3-pyrroline-1-carboxamido)-6-(methylaminothiocarbonylaminosulfonyl)-7-ethylchroman,
3-(2-Oxo-3-pyrroline-1-carboxamido)-6-(methylaminocarbonylaminosulfonyl)-7-ethylchroman,
3-(2-Oxo-3-pyrroline-1-carboxamido)-6-(methylaminothiocarbonylaminosulfonyl)-7-ethoxychroman,
3-(2-Oxo-3-pyrroline-1-carboxamido)-6-(methylaminocarbonylaminosulfonyl)-7-ethoxychroman.

EXAMPLES

Example 1

3-(5-Chloro-2-methoxybenzamido)-6-(methylaminocarbonylaminosulfonyl)-7-methoxychroman

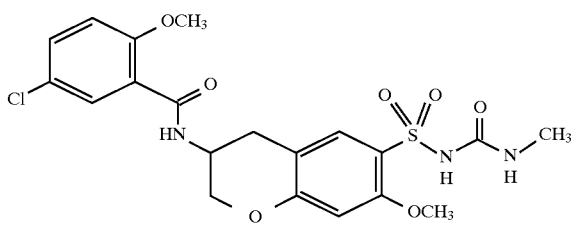

1.71 g (4 mmol) of 3-(5-chloro-2-methoxybenzamido)-6-sulfamoyl-7-methoxychroman were heated at 80° C. for 30 minutes in 10 ml of dry DMSO after addition of 0.4 g (10 mmol) of freshly powdered sodium hydroxide and 1.05 g (6 mmol) of N-methyltrichloroacetamide. The cooled reaction mixture was introduced into ice-water, clarified with active charcoal and acidified to pH 1. The precipitate was filtered off with suction, dried and recrystallized twice from ethanol. The product had a melting point of 256°–257° C.

Preparation of the Starting Compound 3-(5-Chloro-2-methoxybenzamido)-6-sulfamoyl-7-methoxychroman

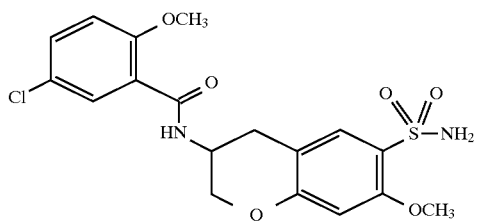

15.1 g (70 mmol) of 3-amino-7-methoxychroman hydrochloride (Eur. J. Med. Chem. 11 (1976), 251–256) were dissolved in 80 ml of pyridine, and 14.8 g of 2-methoxy-5-chlorobenzoyl chloride were added at 0° C. The mixture was stirred at room temperature for 1.5 hours and at 60° C. for 1 hour. The cooled reaction mixture was partitioned between water and methylene chloride. The aqueous phase was extracted three times with methylene chloride. The combined organic phases were washed with 2N hydrochloric acid, water and bicarbonate solution. After drying and evaporation of the organic phase, the residue was dissolved in a little toluene and the product was precipitated with excess diethyl ether. 3-(5-chloro-2-methoxybenzamido)-7-methoxychroman of melting point 92°–93° C. was obtained.

20 g of 3-(5-chloro-2-methoxybenzamido)-7-methoxychroman were introduced in portions into 35 ml of chlorosulfonic acid, cooled to −10° C., while stirring. The mixture was allowed to come to room temperature and a further 5 ml of chlorosulfonic acid were added. After 1 hour, the mixture was stirred cautiously into ice-water. The resulting precipitate was filtered off with suction and, after washing with water, introduced into a mixture, cooled to −20° C., of 200 ml of acetone and 120 ml of concentrated aqueous ammonia. The mixture was allowed to warm to room temperature. After standing overnight, the solution was concentrated at 30° C. in vacuo. Concentrated hydrochloric acid was added to the residue, while cooling with ice. The resulting precipitate was filtered off with suction and recrystallized from glacial acetic acid/methanol. The resulting 3-(5-chloro-2-methoxybenzamido)-6-sulfamoyl-7-methoxychroman had a melting point of 210°–212° C.

Example 2

3-(5-Chloro-2-methoxybenzamido)-6-(ethylaminocarbonylaminosulfonyl)-7-methoxychroman

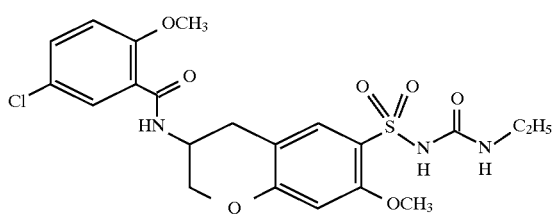

The compound was prepared analogously to Example 1 with 1.15 g (6 mmol) of N-ethyltrichloroacetamide instead of the N-methyltrichloroacetamide and, after recrystallization from ethanol, had a melting point of 233°–234° C.

Example 3

3-(5-Chloro-2-methoxybenzamido)-6-(n-propylamino-carbonylaminosulfonyl)-7-methoxychroman

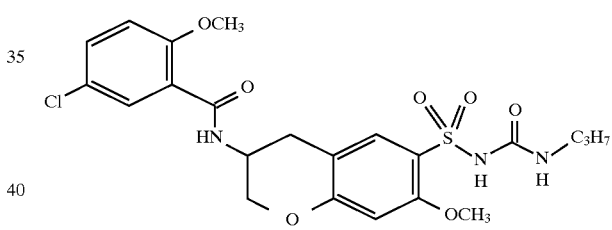

The compound was prepared analogously to Example 1 with 1.23 g (6 mmol) of N-n-propyltrichloroacetamide instead of the N-methyltrichloroacetamide and, after recrystallization from ethyl acetate, had a melting point of 203°–205° C.

Example 4

3-(5-Chloro-2-methoxybenzamido)-6-(isopropylaminocarbonylaminosulfonyl)-7-methoxychroman

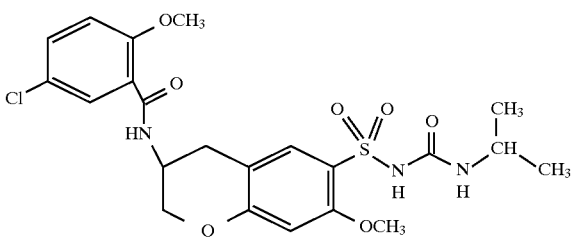

The compound was prepared analogously to Example 1 with 1.23 g (6 mmol) of N-isopropyltrichloroacetamide instead of the N-methyltrichloroacetamide and, after recrystallization from methanol, had a melting point of 181°–183° C.

Example 5

3-(5-Chloro-2-methoxybenzamido)-6-(n-butylaminocarbonylaminosulfonyl)-7-methoxychroman

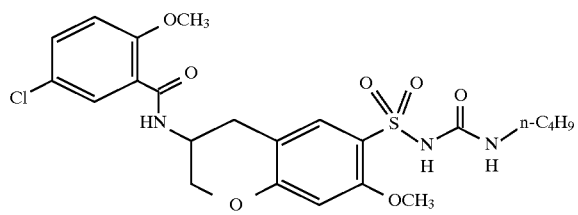

The compound was prepared analogously to Example 1 with 1.31 g (6 mmol) of N-n-butyltrichloroacetamide instead of the N-methyltrichloroacetamide and, after recrystallization from methanol, had a melting point of 185°–186° C.

Example 6

3-(5-Chloro-2-methoxybenzamido)-6-(methylaminothiocarbonylaminosulfonyl-7-methoxychroman

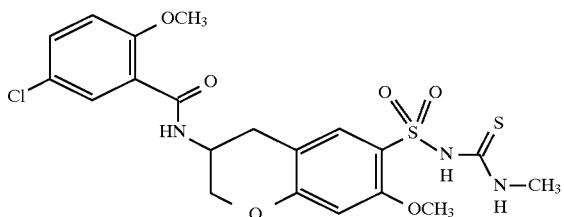

1.71 g (4 mmol) of 3-(5-chloro-2-methoxybenzamido)-6-sulfamoyl-7-methoxychroman (Example 1) were dissolved in 10 ml of dry DMSO, and 1.65 g (12 mmol) of finely powdered potassium carbonate and 0.35 g (4.8 mmol) of methyl isothiocyanate were added. After the mixture had been stirred at 80° C. for 25 minutes, it was cooled, introduced into ice-water, clarified with charcoal and acidified to pH 1. The precipitate was filtered off with suction, dried and recrystallized from ethanol/DMF. Melting point: 219°–220° C.

Example 7

3-(5-Chloro-2-methoxybenzamido)-6-(ethylaminothiocarbonylaminosulfonyl)-7-methoxychroman

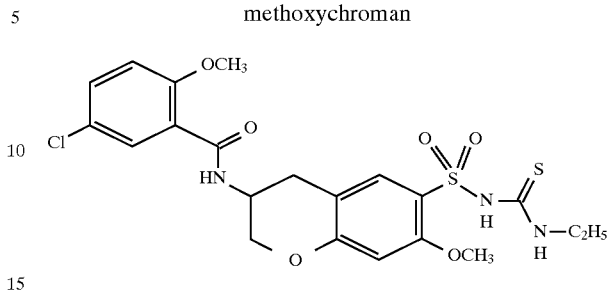

The compound was prepared analogously to Example 6 with 0.41 g (4.8 mmol) of ethyl isocyanate instead of the methyl isothiocyanate and, after recrystallization from methanol/DMF, had a melting point of 194°–195° C.

Example 8

3-(5-Chloro-2-methoxybenzamido)-6-(n-propylamino-thiocarbonylaminosulfonyl)-7-methoxychroman

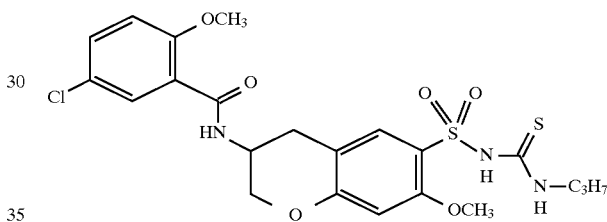

The compound was prepared analogously to Example 6 with 0.5 ml (4.8 mmol) of n-propyl isocyanate instead of the methyl isothiocyanate and, after recrystallization from ethanol/DMF, had a melting point of 182° C.

Example 9

3-(5-Fluoro-2-methoxybenzamido)-6-(methylaminocarbonylaminosulfonyl)-7-methoxychroman

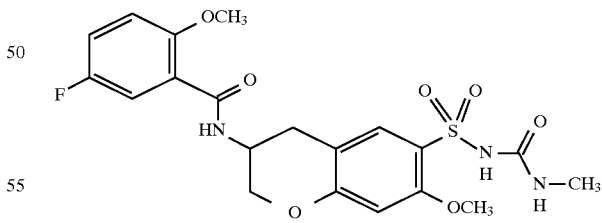

1.64 g (4 mmol) of 3-(5-fluoro-2-methoxybenzamido)-6-sulfamoyl-7-methoxychroman were heated at 80° C. for 30 minutes in 10 ml of dry DMSO after addition of 0.4 g (10 mmol) of freshly powdered sodium hydroxide and 1.05 g (6 mmol) of N-methyltrichloroacetamide. The cooled reaction mixture was introduced into ice-water, clarified with active charcoal and acidified to pH 1. The precipitate was filtered off with suction, dried and recrystallized from ethanol. The product had a melting point of 260° C.

Preparation of the Starting Compound 3-(5-Fluoro-2-methoxybenzamido)-6-sulfamoyl-7-methoxychroman

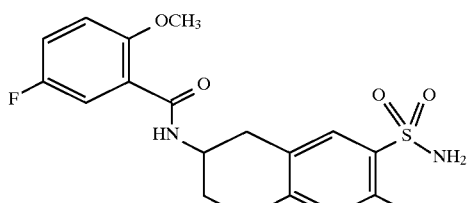

13.6 g (72 mmol) of 2-methoxy-5-fluoro-benzoyl chloride were added to 15.1 g (70 mmol) of 3-amino-7-methoxychroman hydrochloride in 80 ml of pyridine cooled to 0° C. Working up was carried out analogously to Example 1. After recrystallization from ethanol, the resulting 3-(5-fluoro-2-methoxybenzamido)-7-methoxychroman had a melting point of 107°–108° C. Further reaction with chlorosulfonic acid and ammonia was carried out analogously to Example 1. After recrystallization from DMF/methanol, the resulting 3-(5-fluoro-2-methoxybenzamido)-6-sulfamoyl-7-methoxychroman had a melting point of 209°–210° C.

Example 10

3-(5-Fluoro-2-methoxybenzamido)-6-(methylaminothiocarbonylaminosulfonyl)-7-methoxychroman

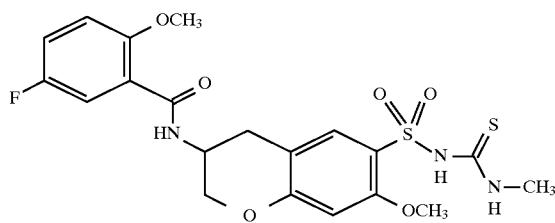

1.65 g (12 mmol) of powdered potassium carbonate and 0.35 g (4.8 mmol) of methyl isothiocyanate were added to 1.64 g (4 mmol) of 3-(5-fluoro-2-methoxybenzamido)-6-sulfamoyl-7-methoxychroman (Example 9) in 10 ml of dry DMSO. After the mixture had been stirred at 80° C. for 25 minutes, it was cooled, introduced into ice-water, clarified with charcoal and acidified to pH 1. The precipitate was filtered off with suction, dried and recrystallized from ethanol. The product had a melting point of 221°–222° C.

Example 11

3-(5-Fluoro-2-methoxybenzamido)-6-ethylaminothiocarbonylaminosulfonyl)-7-methoxychroman

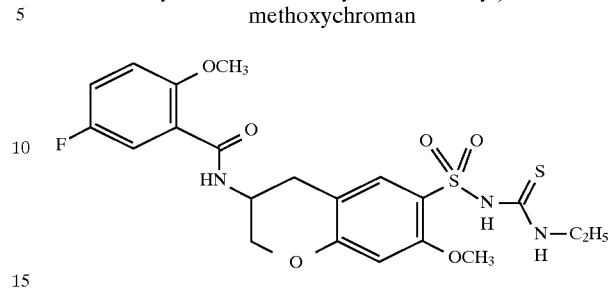

The compound was prepared analogously to Example 10 with 0.41 g (4.8 mmol) of ethyl isothiocyanate instead of the methyl isothiocyanate and had a melting point of 186°–187° C.

Example 12

3-(5-Fluoro-2-methoxybenzamido)-6-(n-propylamino-thiocarbonylaminosulfonyl)-7-methoxychroman

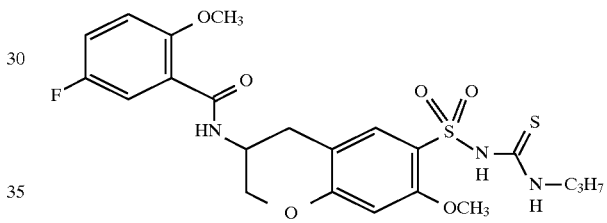

The compound was prepared analogously to Example 10 with 0.5 ml (4.8 mmol) of n-propyl isothiocyanate instead of the methyl isothiocyanate and, after recrystallization from ethanol, had a melting point of 172°–173° C.

Example 13

3-(5-Fluoro-2-methoxybenzamido)-6-(isopropylaminothiocarbonylaminosulfonyl)-7-methoxychroman

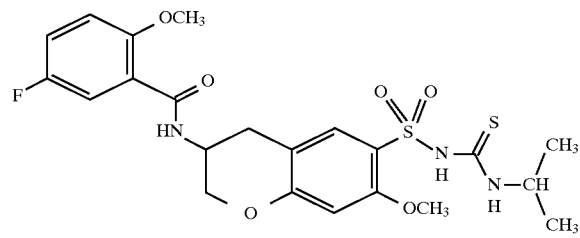

The compound was prepared analogously to Example 10 with 0.48 ml of isopropyl isothiocyanate instead of the methyl isothiocyanate and, after recrystallization from ethanol, had a melting point of 179°–180° C.

Example 14

3-(5-Chloro-2-methoxybenzamido)-6-(methylaminothiocarbonylaminosulfonyl)-7-methylchroman

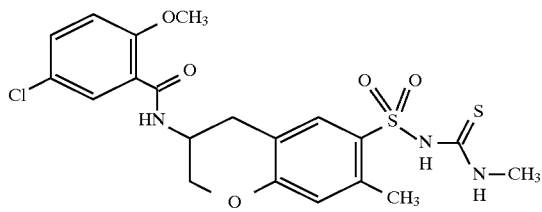

1.64 g (4 mmol) of 3-(5-chloro-2-methoxybenzamido)-6-sulfamoyl-7-methylchroman were dissolved in 10 ml of dry DMSO, and 1.65 g (12 mmol) of finely powdered potassium carbonate and 0.35 g (4.8 mmol) of methyl isothiocyanate were added. After the mixture had been stirred at 80° C. for 25 minutes, it was cooled, introduced into ice-water, clarified with charcoal and acidified to pH 1. The precipitate was filtered off with suction, dried, purified over a silica gel column using ethyl acetate/toluene 2:1 and recrystallized from ethanol. Melting point: 207°–208° C.

Preparation of the Starting Compound 3-(5-chloro-2-methoxybenzamido)-6-sulfamoyl-7-methylchroman a) 3-(5-Chloro-2-methoxybenzamido)-7-methyl-4-chromanone

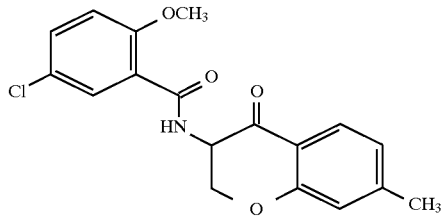

17.5 g (85 mmol) of 5-chloro-2-methoxybenzoyl chloride were added to a solution of 18.2 g (85 mmol) of 3-amino-7-methyl-4-chromanone hydrochloride (Hebd. Seances Acad. Sci. Ser. C. 279, 281–284) in 90 ml of pyridine at room temperature. After the mixture had been stirred for 2 hours (TLC control: silica gel plate using petroleum ether/ethyl acetate/toluene 2:2:1), it was introduced into ice/water. The precipitate was filtered off with suction, washed several times with water and dried. The 3-(5-chloro-2-methoxybenzamido)-7-methyl-4-chromanone had a melting point of 177°–178° C.

b) 3-(5-Chloro-2-methoxybenzamido)-7-methylchroman-4-ol

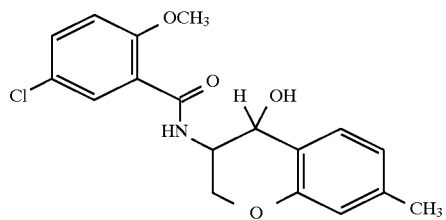

0.5 g (12.5 mmol) of sodium borohydride was introduced into a suspension of 8.65 g (25 mmol) of 3-(5-chloro-2-methoxybenzamido)-7-methyl-4-chromanone in 40 ml of ethanol. During stirring at 30°–40° C. for 2 hours, the solid dissolved. The solution was then cooled, introduced into ice/water and acidified to pH 1–2 with dilute hydrochloric acid. The precipitate was filtered off with suction, washed with water, dried and recrystallized from ethanol. The resulting 3-(5-chloro-2-methoxybenzamido)-7-methylchroman-4-ol (diastereomer mixture) had a melting point of 151°–152° C.

c) 3-(5-Chloro-2-methoxybenzamido)-7-methylchroman

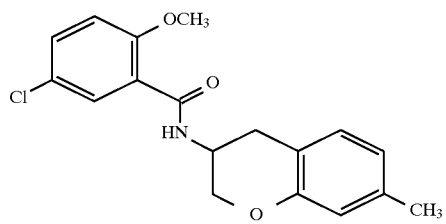

7.7 g (22 mmol) of 3-(5-chloro-2-methoxybenzamido)-7-methylchroman-4-ol were hydrogenated in a mixture of 80 ml of glacial acetic acid, 7.5 ml of acetic anhydride and 0.5 ml of trifluoroacetic acid with 0.5 g of Pd/C (10 %) at 25° C. under atmospheric pressure for about 3 hours. The catalyst was filtered off and the filtrate was concentrated to a small volume in vacuo. The residue was introduced into ice/water and the mixture was extracted several times with methylene chloride. The combined methylene chloride extracts were washed with sodium bicarbonate solution and water, dried and concentrated and the residue was recrystallized from diisopropyl ether. The 3-(5-chloro-2-methoxybenzamido)-7-methylchroman had a melting point of 97° C.

d) 3-(5-Chloro-2-methoxybenzamido)-6-sulfamoyl-7-methylchroman

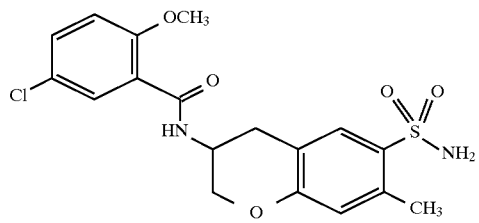

5.8 g of 3-(5-chloro-2-methoxybenzamido)-7-methylchroman were stirred into 10 ml of chlorosulfonic acid, with gentle cooling. After the mixture had been stirred at room temperature for about 45 minutes, it was cautiously added dropwise to ice/water. The precipitate was filtered off with suction and introduced into a mixture, cooled to about −10° C., of 50 ml of acetone and 30 ml of concentrated aqueous ammonia. The mixture was allowed to come to room temperature and was subsequently stirred for 3 hours, and the solution was concentrated at 30° C. in vacuo. The residue was acidified with concentrated hydrochloric acid, while cooling with ice. The precipitate was filtered off with suction, washed neutral with water and recrystallized from glacial acetic acid/methanol. The 3-(5-chloro-2-methoxybenzamido)-6-sulfamoyl-7-methylchroman had a melting point at 218°–219° C.

Example 15

3-(5-Chloro-2-methoxybenzamido)-2,2-dimethyl-6-(methylaminocarbonylaminosulfonyl)-7-methoxychroman

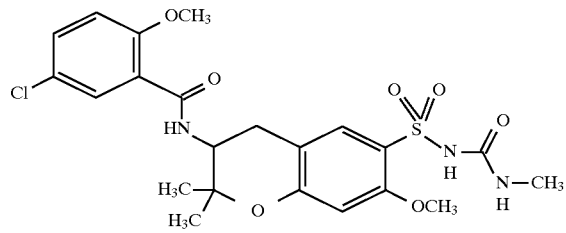

1.23 g (7.5 mmol) of N-methyltrichloroacetamide were added to 2.27 g (5 mmol) of 3-(5-chloro-2-methoxybenzamido)-2,2-dimethyl-6-sulfamoyl-7-methoxychroman and 0.5 g (12.5 mmol) of finely powdered sodium hydroxide. After the mixture had been stirred at 80° C. for half an hour, it was introduced into ice/water, clarified with charcoal and acidified to pH 1. The precipitate was filtered off with suction, dried and recrystallized from ethanol/DMF. The product had a melting point of 248° C.

Preparation of the Starting Compound 3-(5-Chloro-2-methoxybenzamido)-2,2-dimethyl-6-sulfamoyl-7-methoxychroman

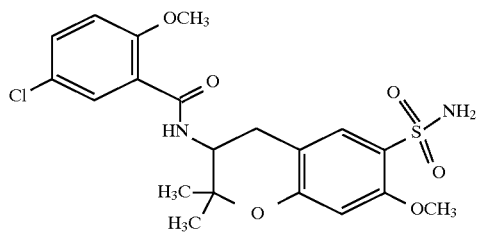

a) 2,2-Dimethyl-7-methoxy-4-chromanone Oxime Tosylate

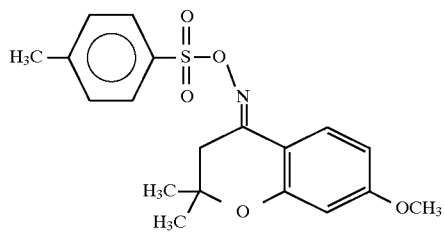

85.8 g (0.45 mol) of p-toluenesulfonyl chloride were introduced into a solution of 88.5 g (0.4 mol) of 2,2-dimethyl-7-methoxy-4-chromanone oxime (Heterocycles 38 (1994), 305–318) in 550 ml of pyridine at 0° C. The mixture was allowed to come to room temperature and was subsequently stirred for several hours, stirred into ice/water and extracted with methylene chloride. The organic solution was washed twice with 2N hydrochloric acid and then several times with water, dried and evaporated, and the residue was recrystallized from ethanol. The 2,2-dimethyl-7-methoxy-4-chromanone oxime tosylate had a melting point of 113° C.

b) 3-Amino-2,2-dimethyl-7-methoxy-4-chromanone Hydrochloride

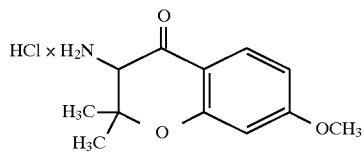

6.9 g (0.3 mol) of sodium were dissolved in 250 ml of ethanol under nitrogen, with gentle cooling. A suspension of 105 g (0.28 mol) of 2,2-dimethyl-7-methoxy-4-chromanone oxime tosylate in 900 ml of ethanol was added to this sodium ethylate solution. The mixture was heated to 50° C., kept at this temperature for 3 hours, heated to 60° C. for 1 hour and cooled, the sodium sulfonate which had precipitated out was filtered off with suction, the filtrate was concentrated, the concentrate was poured into ice-water acidified with hydrochloric acid, the mixture was extracted twice with methylene chloride and the aqueous solution was clarified with charcoal. On concentration, 3-amino-2,2-dimethyl-7-methoxy-4-chromanone hydrochloride precipitated out. Melting point: 224°–226° C.

c) 3-(5-Chloro-2-methoxybenzamido)-2,2-dimethyl-7-methoxy-4-chromanone

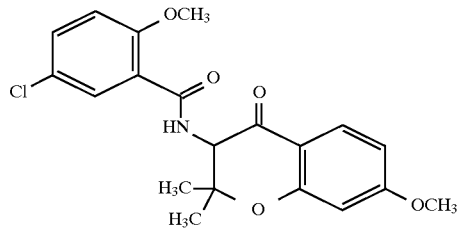

28.7 g (0.14 mol) of 5-chloro-2-methoxybenzoyl chloride were introduced into a solution of 33.5 g (0.13 mol) of 3-amino-2,2-dimethyl-7-methoxy-4-chromanone hydrochloride in 150 ml of pyridine at 10° C. After the mixture had been stirred at about 27° C. for three hours, it was introduced into ice/water and extracted twice with methylene chloride. The combined methylene chloride extracts were washed twice with 2N hydrochloric acid and with water and then dried and evaporated, and the residue was recrystallized from ethanol/DMF. The 3-(5-chloro-2-methoxybenzamido)-2,2-dimethyl-7-methoxy-4-chromanone had a melting point of 174° C.

d) 3-(5-Chloro-2-methoxybenzamido)-2,2-dimethyl-7-methoxy-4-chromanol

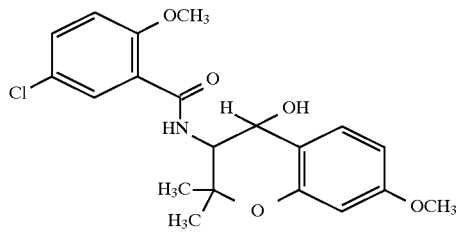

A suspension of 25 g (64 mmol) of 3-(5-chloro-2-methoxybenzamido)-2,2-dimethyl-7-methoxy-4-chromanone and 1.24 g (32 mmol) of powdered sodium borohydride in 100 ml of ethanol was stirred at 50° C. for 3 hours, during which the solid dissolved. After cooling, the solution was then poured into ice-water acidified with hydrochloric acid, and extracted with methylene chloride. The organic solution was washed with water, dried and evaporated. The resulting 3-(5-chloro-2-methoxybenzamido)-2,2-dimethyl-7-methoxy-4-chromanol (diastereomer mixture) melted from 165° C.

e) 3-(5-Chloro-2-methoxybenzamido)-2,2-dimethyl-7-methoxychroman

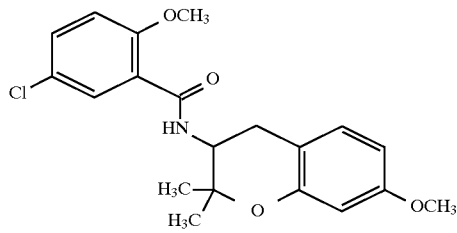

44 g (300 mmol) of sodium iodide and 38 ml (300 mmol) of chlorotrimethylsilane were added to 19.6 g (50 mmol) of 3-(5-chloro-2-methoxybenzamido)-2,2-dimethyl-7-methoxy-4-chromanol in 120 ml of acetonitrile. The temperature rose temporarily to 32° C. After the mixture had been stirred at about 25° C. for three hours, it was poured into ice/water, decolorized with concentrated sodium bisulfite solution and extracted several times with methylene chloride. The combined organic solutions were washed with water, dried and evaporated and the residue was chromatographed over a silica gel column using methylene chloride/ethyl acetate 95:5. The 3-(5-chloro-2-methoxybenzamido)-2,2-dimethyl-7-methoxychroman was obtained as an oil.

f) 3-(5-Chloro-2-methoxybenzamido)-2,2-dimethyl-7-methoxy-6-sulfamoyl-chroman

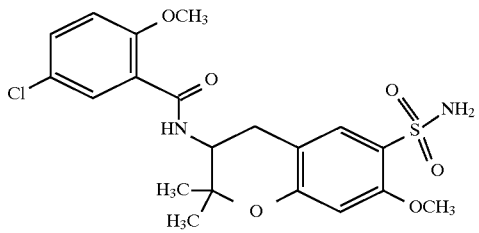

18 g (47.9 mmol) of 3-(5-chloro-2-methoxybenzamido)-2,2-dimethyl-7-methoxychroman were cooled to below 0° C., and 25 ml of chlorosulfonic acid cooled to −15° C. were added. On warming to 10° C., the temperature rose rapidly to 35° C. The mixture was cooled to 0° C. and then stirred at 15° C. for 2 hours and introduced into ice-water, and the sulfochloride was filtered off with suction and introduced into a mixture, cooled to −10° C., of 350 ml of acetone and 75 ml of concentrated aqueous ammonia. The mixture was allowed to come to room temperature and was subsequently stirred for several hours, and the solution was concentrated in vacuo at 30° C. The residue was acidified with concentrated hydrochloric acid, while cooling with ice. The precipitate was filtered off with suction, washed neutral with water, dried and recrystallized from ethanol. The 3-(5-chloro-2-methoxybenzamido)-2,2-dimethyl-7-methoxy-6-sulfamoyl-chroman had a melting point of 228° C.

Example 16

3-(5-Chloro-2-methoxybenzamido)-2,2-dimethyl-6-(methylaminothiocarbonylaminosulfonyl)-7-methoxychroman

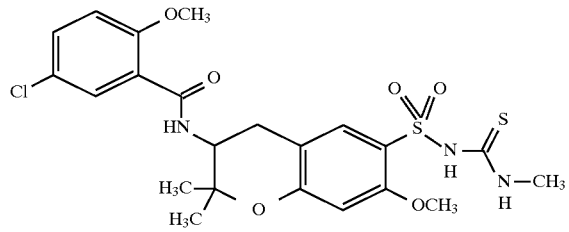

0.26 g (3.5 mmol) of methyl isothiocyanate was added to a suspension of 1.14 g (2.5 mmol) of 3-(5-chloro-2-methoxybenzamido)-2,2-dimethyl-6-sulfamoyl-7-methoxychroman and 1.04 g (7.5 mmol) of finely powdered potassium carbonate in 10 ml of DMSO. After the mixture had been stirred at 80° C. for 25 minutes, it was cooled, introduced into ice/water, clarified with charcoal and acidified to pH 1. The precipitate was filtered off with suction and recrystallized from methanol/DMF. The product had a melting point of 234°–235° C.

Example 17

3-(5-Chloro-2-methoxybenzamido)-2,2-dimethyl-6-(n-propylaminothiocarbonylaminosulfonyl)-7-methoxychroman

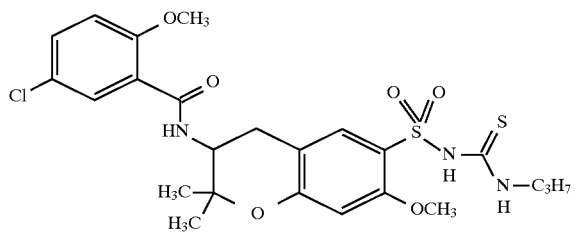

The compound was prepared analogously to Example 16 with 0.36 ml (3.5 mmol) of n-propyl isothiocyanate instead of the methyl isothiocyanate and, after recrystallization from methanol/DMF, had a melting point of 210°–211° C.

Example 18

3-(5-Chloro-2-methoxybenzamido)-2,2-dimethyl-6-(isopropylaminothiocarbonylaminosulfonyl)-7-methoxychroman

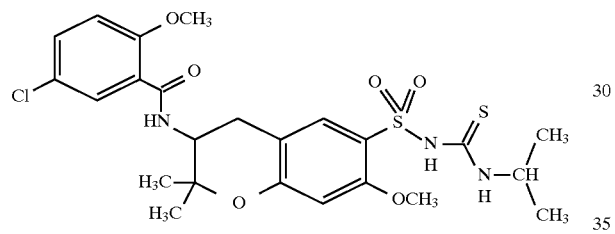

The compound was prepared analogously to Example 16 with 0.35 ml (3.5 mmol) of isopropyl isothiocyanate instead of the methyl isothiocyanate and, after recrystallization from methanol/DMF, had a melting point of 201°–202° C.

Example 19

3-(5-Fluoro-2-methoxybenzamido)-2,2-dimethyl-6-(methylaminothiocarbonylaminosulfonyl)-7-methoxychroman

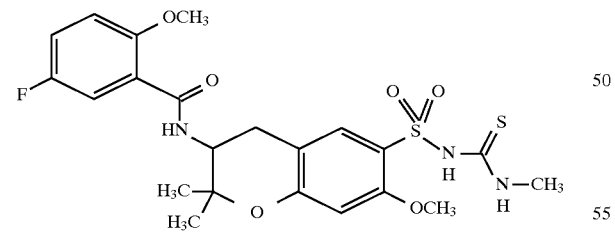

0.26 g (3.5 mmol) of methyl isothiocyanate was added to a suspension of 1.1 g (2.5 mmol) of 3-(5-fluoro-2-methoxybenzamido)-2,2-dimethyl-7-methoxy-6-sulfamoyl-chroman and 1.04 g (7.5 mmol) of finely powdered potassium carbonate in 10 ml of DMSO. After the mixture had been stirred at 80° C. for 25 minutes, it was cooled, introduced into ice/water, clarified with charcoal and acidified to pH 1. The precipitate was filtered off with suction and recrystallized from ethanol/DMF. The product had a melting point of 222° C.

Preparation of the Starting Compound 3-(5-Fluoro-2-methoxybenzamido)-2,2-dimethyl-6-sulfamoyl-7-methoxychroman

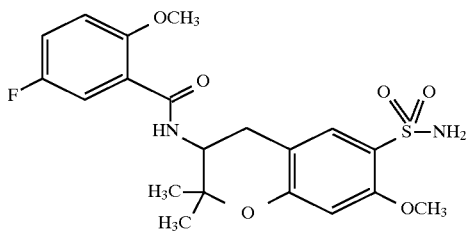

a) 3-(5-Fluoro-2-methoxybenzamido)-2,2-dimethyl-7-methoxy-4-chromanone

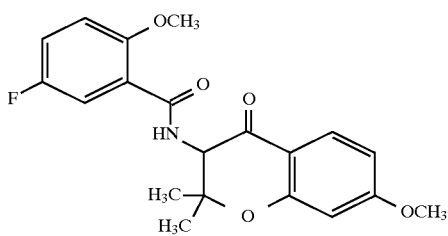

The compound was prepared analogously to Example 15c with 26.4 g (0.14 mol) of 5-fluoro-2-methoxybenzoyl chloride instead of the 5-chloro-2-methoxybenzoyl chloride and, after recrystallization from ethanol/DMF, had a melting point of 143°–144° C.

b) 3-(5-Fluoro-2-methoxybenzamido)-2,2-dimethyl-7-methoxy-4-chromanol

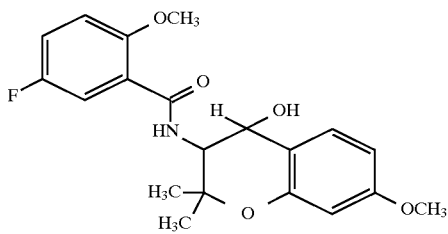

The compound was prepared analogously to Example 15d using 23.9 g (64 mmol) of 3-(5-fluoro-2-methoxybenzamido)-2,2-dimethyl-7-methoxy-4-chromanone. After reduction with sodium borohydride, 3-(5-fluoro-2-methoxybenzamido)-2,2-dimethyl-7-methoxy-4-chromanol was obtained as a diastereomer mixture of melting point 156°–157° C.

c) 3-(5-Fluoro-2-methoxybenzamido)-2,2-dimethyl-7-methoxy-4-chroman

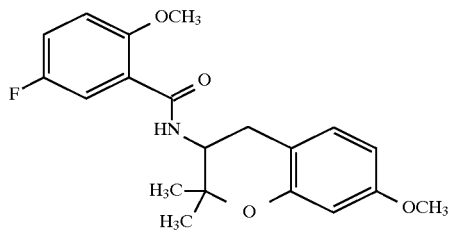

A reduction was carried out analogously to Example 15e using 18.8 g (50 mmol) of 3-(5-fluoro-2-methoxybenzamido)-2,2-dimethyl-7-methoxy-4-chromanol. After chromatography over a silica gel column using methylene chloride/ethyl acetate 95:5, the 3-(5-fluoro-2-methoxybenzamido)-2,2-dimethyl-7-methoxychroman was obtained as an oil.

d) 3-(5-Fluoro-2-methoxybenzamido)-2,2-dimethyl-7-methoxy-6-sulfamoyl-chroman

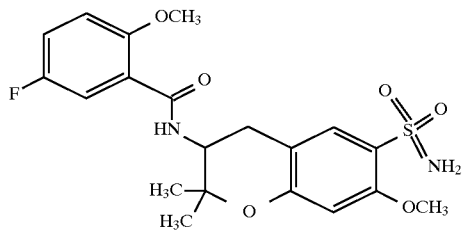

The compound was prepared analogously to Example 15 f using 17.2 g (47.9 mmol) of 3-(5-fluoro-2-methoxybenzamido)-2,2-dimethyl-7-methoxy-4-chroman and, after recrystallization from ethanol, had a melting point of 159°–160° C.

Example 20

3-(5-Fluoro-2-methoxybenzamido)-2,2-dimethyl-6-(ethylaminothiocarbonylaminosulfonyl)-7-methoxychroman

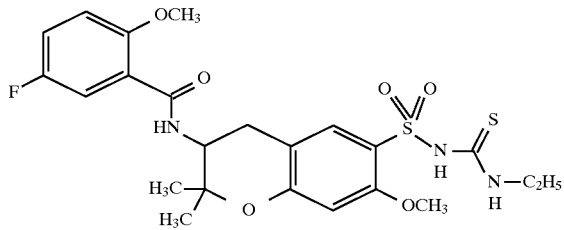

The compound was prepared analogously to Example 19 with 0.31 ml (35 mmol) of ethyl isothiocyanate instead of the methyl isothiocyanate and had a melting point of 211° C.

Example 21

3-(5-Fluoro-2-methoxybenzamido)-2,2-dimethyl-6-(isopropylaminothiocarbonylaminosulfonyl)-7-methoxychroman

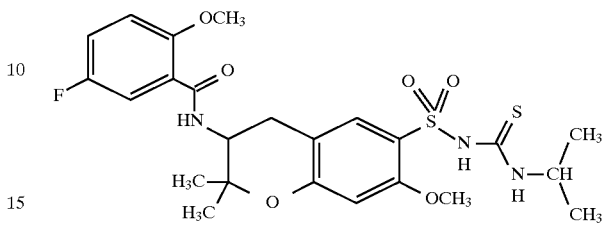

The compound was prepared analogously to Example 19 with 0.35 ml (35 mmol) of isopropyl isothiocyanate instead of the methyl isothiocyanate and had a melting point of 156°–157° C.

Example 22

3-(3-Ethyl-4-methyl-2-oxo-3-pyrroline-1-carboxamido)-6-(methylaminothiocarbonylaminosulfonyl)-7-methoxychroman

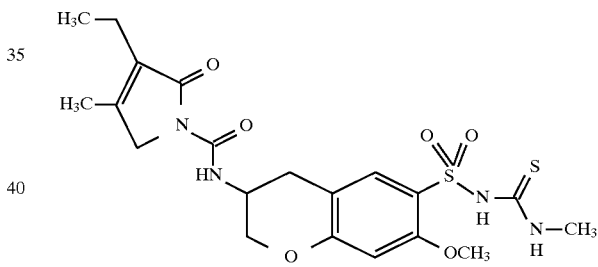

2.05 g (5 mmol) of 3-(3-ethyl-4-methyl-2-oxo-3-pyrroline-1-carboxamido)-6-sulfamoyl-7-methoxychroman, 2.07 g (15 mmol) of finely powdered potassium carbonate and 0.44 g (6 mmol) of methyl isothiocyanate were suspended or dissolved in 20 ml of DMSO. The reaction mixture was stirred at 80° C. for 1 hour. The mixture was poured onto ice-water and the product was precipitated by acidification with hydrochloric acid. After the crude product had been filtered off with suction and dried, it was purified by chromatography over silica gel (eluting agent methylene chloride/glacial acetic acid 19:1). The product had a melting point of 205° C.

Preparation of the Starting Compound 3-(3-Ethyl-4-methyl-2-oxo-3-pyrroline-1-carboxamido)-6-sulfamoyl-7-methoxychroman

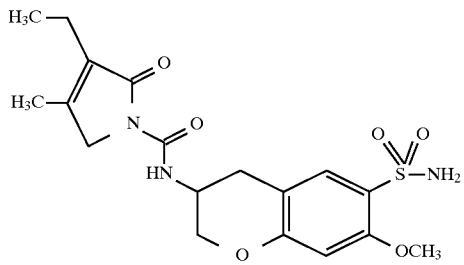

8.43 g (52 mmol) of N,N'-carbonyldiimidazole were added to a solution of 8.2 g (46 mmol) of 3-amino-7-methoxychroman in 60 ml of THF. During this operation, the solution became warm. After the solution had been stirred at room temperature for one hour, it was evaporated in vacuo. The residue was melted together with 6.51 g (52 mmol) of 3-ethyl-4-methyl-3-pyrrolin-2-one at 160°–170° C. for 1.5 to 2 hours and the mixture was then chromatographed over silica gel using the eluting agent ethyl acetate/petroleum ether 3:1. The main fraction was evaporated and the residue was recrystallized from methanol. 3-(3-Ethyl-4-methyl-2-oxo-3-pyrroline-1-carboxamido)-7-methoxychroman of melting point 118°–119° C. was obtained. This product was introduced by the customary procedure into chlorosulfonic acid which had been cooled to −15° C. The mixture was allowed to come to room temperature and was subsequently stirred for 1 hour. After customary work-up, the sulfochloride was converted into the sulfonamide as described in Example 1. 3-(3-Ethyl-4-methyl-2-oxo-3-pyrroline-1-carboxamido)-6-sulfamoyl-7-methoxychroman had a melting point of 225°–227° C.

Example 23

3-(3-Ethyl-4-methyl-2-oxo-3-pyrroline-1-carboxamido)-6-(methylaminocarbonylaminosulfonyl)-7-methoxychroman

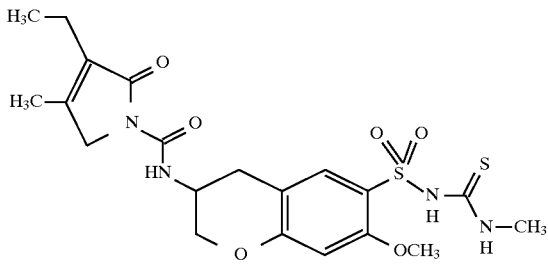

1 g of 3-(3-ethyl-4-methyl-2-oxo-3-pyrroline-1-carboxamido)-6-(methylaminothiocarbonylaminosulfonyl)-7-methoxychroman (Example 22) was suspended or dissolved in 20 ml of cold 0.5N sodium hydroxide solution. 1 ml of 37% strength hydrogen peroxide solution was added in the cold (−4° to 0° C.). The mixture was stirred at 0° C. for 1.5 hours. The crude product was precipitated by addition of 2N HCl and then purified over silica gel (eluting agent methylene chloride/glacial acetic acid 9:1). The product had a melting point of 245°–246° C.

Pharmacological Data

The therapeutic properties of the compounds of the formula I were demonstrated in the following models:

Test 1: Duration of the action potential of the papillary muscle of the guinea pig (a) Introduction ATP deficiency states such as are observed in the cardiac muscle cell during ischemia lead to a shortening of the duration of the action potential. They are regarded as one of the causes of so-called "re-entry arrhythmias," which can cause sudden cardiac death. The opening of ATP-sensitive potassium channels as a result of the fall in ATP is regarded as the cause of this.

(b) Method

A standard microelectrode technique was employed to measure the action potential. For this, guinea pigs of both sexes were sacrificed by a blow to the head, the hearts were removed and the papillary muscles were separated out and suspended in an organ bath. The organ bath was flushed with Ringer's solution (0.9% NaCl, 0.048% KCl, 0.024% $CaCl_2$, 0.02% $NaHCO_3$ and 0.1% glucose) and gassed with a mixture of 95% oxygen and 5% carbon dioxide at a temperature of 36° C. The muscle was stimulated via an electrode with rectangular pulses of 1 V and 1 ms duration and a frequency of 2 Hz. The action potential was derived through a glass microelectrode which was inserted intracellularly and filled with 3M KCl solution, and recorded. The substances to be tested were added to the Ringer's solution in a concentration of $2 \times 10^{-6}$ mol per liter or $2 \times 10^{-5}$ mol per liter. The action potential was amplified with a Hugo Sachs amplifier and shown on an oscilloscope. The duration of the action potential in milliseconds (ms) was determined at a degree of repolarization of 95% ($APD_{95}$). Shortenings of the action potential were induced by addition of a solution of the potassium channel opener HOE 234 (Rilmakalim) (W. Linz, E. Klaus, U. Albus, R. H. A. Becker, D. Mania, H. C. Englert, B. A. Scholkens, Arzneimittelforschung/Drug Research, Volume 42 (II), 1992, 1180–1185), a concentration of HOE 234 in the bath solution of 1 μg/ml being established. The test substances were added to the bath solution as stock solutions in propanediol. The values stated are based on measurements 30 minutes after the addition. As a control, the $APD_{95}$ value was determined in the presence of HOE 234 and in the absence of the test substance.

(c) Results

The following values were measured:

| Compound | Concentration | $APD_{95}$-HOE 234 (ms) | | |
|---|---|---|---|---|
| Control | | <40 | | |
| Example 1 | 20 μmol/l | 157 ± 36 | (158 ± 12) | (n = 3) |
| Example 3 | 20 μmol/l | 134 ± 9 | (178 ± 8) | (n = 3) |
| Example 6 | 2 μmol/l | 145 ± 19.1 | (187 ± 10.2) | (n = 3) |
| Example 7 | 2 μmol/l | 130 ± 28.1 | (173 ± 13.1) | (n = 3) |
| Example 21 | 2 μmol/l | 67 ± 10 | (149 ± 3) | (n = 3) |

The measurement values (mean values from n experiments) are followed by the corresponding blank values in parentheses. The blank values are the $APD_{95}$ values which were measured at the start of the experiment without HOE 234 and test substance in the Ringer's solution. The values obtained show the normalizing effect of the compounds according to the invention on a shortened duration of the action potential.

Test 2: Membrane potential on isolated β cells (a) Introduction

The action mechanism of hypoglycemic sulfonylureas is understood in principle. The β cells of the pancreas are the target organ of sulfonylureas, where they bring about a release of the hypoglycemic hormone insulin by influencing the electrical potential of the cell membrane. A hypoglycemic sulfonylurea, for example glibenclamide, has the effect of depolarizing the cell membrane, which leads to an increased inflow of calcium ions and, as a consequence thereof, to the release of insulin. The extent ΔU of this depolarization of the cell membrane caused by the substances according to the invention was determined on insulin-secreting RINm5F cells, a pancreas tumor cell line. The activity of a compound in this model predicts the extent of the hypoglycemic potential of this compound.

(b) Method

Cell cultures of RINm5F cells: RINm5F cells were cultured at 37° C. in RPMI 1640 culture medium (Flow) to which 11 mM glucose, 10% (volume/volume) fetal calf serum, 2 mM glutamine and 50 μg/ml of gentamycin were added. The cells were sown on Petri dishes every 2 to 3 days and kept at a temperature of 37° C. in a moistened atmosphere of 95% $O_2$ and 5% $CO_2$. For the investigations, the cells were isolated by incubation (about 3 minutes) in a $Ca^{2+}$-free medium which comprised 0.25% trypsin.

Measurement method: Isolated RINm5F cells were introduced into a Plexiglas chamber on an inverse microscope which was equipped with a differential interference contrast lens. Under visual control (400-fold magnification), a fire-polished micropipette with an opening diameter of about 1 μm was placed on the cell with the aid of a micromanipulator. By applying a slight reduced pressure to the inside of the patch pipette, a high electrical seal was initially established between the glass and the cell membrane. By increasing the reduced pressure, the membrane patch under the volumetric pipette was then broken open. In this whole cell configuration, the cell potential was recorded with the aid of a patch clamp amplifier (L/M EPC 7, List, Darmstadt) and the whole cell current was measured by applying a voltage ramp. The patch pipette was filled with KCl solution which comprised (in mmol per liter): 140 KCl, 10 NaCl, 1.1 $MgCl_2$, 0.5 EGTA, 1 Mg-ATP, and 10 HEPES, and had a pH of 7.2. The bath contained NaCl solution which comprised (in mmol per liter): 140 NaCl, 4.7 KCl, 1.1 $MgCl_2$, 2 $CaCl_2$ and 10 HEPES, and had a pH of 7.4. Stock solutions (concentration 100 mmol/l) of the test substances in dimethyl sulfoxide (DMSO) and corresponding dilutions in NaCl solution were prepared. DMSO alone had no effect on the cell potential. To stabilize the cell potential, diazoxide (100 μmol/l), an opener of ATP-sensitive $K^+$ channels, was added to the bath solution in all experiments. All experiments were carried out at 34°±1° C.

(c) Results

The following values ΔU (changes in the cell potentials caused by the addition of the test substances) were measured. The control values in parentheses are the cell potentials U before the addition of the test substances. For comparison the values obtained in this test with glibenclamide, a typical hypoglycemic benzenesulfonylurea, are given. The values obtained show that the compounds according to the invention exhibit no or only a low hypoglycemic activity.

| Compound | Concentration | ΔU (mV) |
| --- | --- | --- |
| Example 1 | 1 μmol/l | 6 (control: −74 mV) |
| Example 1 | 10 μmol/l | 24 (control: −74 mV) |
| Example 3 | 1 μmol/l | 18 (control: −69 mV) |
| Example 3 | 10 μmol/l | 23 (control: −69 mV) |
| Example 6 | 1 μmol/l | 3 (control: −76 mV) |
| Example 7 | 1 μmol/l | 29 (control: −78 mV) |
| Glibenclamide | 1 μmol/l | 47 (control: −73 mV) |
| Glibenclamide | 10 μmol/l | 46 (control: −73 mV) |

What is claimed is:

1. A compound of the formula (I)

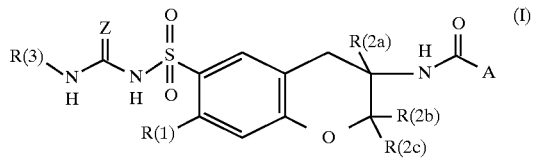

in which:

R(1) is hydrogen, alkyl having 1, 2, 3 or 4 carbon atoms, alkoxy having 1, 2, 3 or 4 carbon atoms, alkoxyalkoxy having 1, 2, 3 or 4 carbon atoms independently of one another in each of the two alkoxy units, alkylmercapto having 1, 2, 3 or 4 carbon atoms, fluorine, chlorine, bromine, iodine or trifluoromethyl;

R(2a), R(2b) and R(2c), which are identical or different, are hydrogen or alkyl having 1 or 2 carbon atoms;

R(3) is hydrogen or alkyl having 1, 2, 3 or 4 carbon atoms;

Z is sulfur or oxygen;

A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

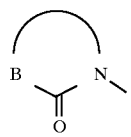

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system selected from the group consisting of the formulae:

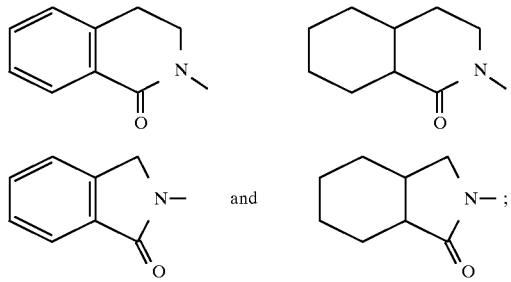

in any of its stereoisomeric forms, or a mixture thereof in any ratio;

or any of its physiologically acceptable salts.

2. A compound of the formula (I) as claimed in claim 1, in which:

R(1) is hydrogen, alkyl having 1 or 2 carbon atoms, alkoxy having 1, 2, 3 or 4 carbon atoms, alkylmercapto having 1, 2, 3 or 4 carbon atoms, fluorine, chlorine, bromine, iodine or trifluoromethyl;

R(2a), R(2b) and R(2c), which are identical or different, are hydrogen or alkyl having 1 or 2 carbon atoms;

R(3) is hydrogen or alkyl having 1, 2, 3 or 4 carbon atoms;

Z is sulfur or oxygen;

A is phenyl which is unsubstituted or substituted by up to three identical or different substituents selected from the group consisting of halogen, alkyl having 1 or 2 carbon atoms and alkoxy having 1 or 2 carbon atoms, or A is the radial of a saturated or unsaturated lactam of the formula

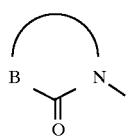

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system selected from the group consisting of the formulae:

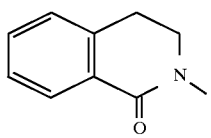 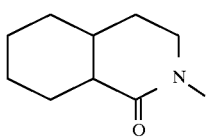

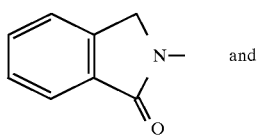 and 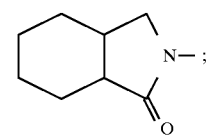 ;

in any of its stereoisomeric forms, or a mixture thereof in any ratio;

or any of its physiologically acceptable salts.

3. A compound of the formula (I) as claimed in claim 1, in which:

R(1) is hydrogen, alkyl having 1 or 2 carbon atoms, alkoxy having 1 or 2 carbon atoms, alkylmercapto having 1 or 2 carbon atoms, fluorine, chlorine, bromine, iodine or trifluoromethyl;

R(2a) is hydrogen and R(2b) and R(2c) are hydrogen or methyl;

R(3) is hydrogen or alkyl having 1, 2, 3 or 4 carbon atoms;

Z is sulfur or oxygen;

A is phenyl which is unsubstituted or substituted by up to three identical or different substituents selected from the group consisting of halogen, alkyl having 1 or 2 carbon atoms and alkoxy having 1 or 2 carbon atoms, or A is the radial of a saturated or unsaturated lactam of the formula

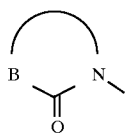

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system selected from the group consisting of the formulae:

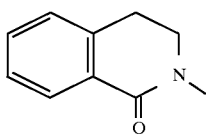 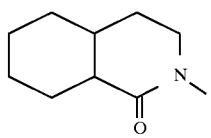

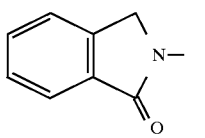 and 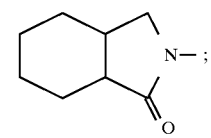 ;

in any of its stereoisomeric forms, or a mixture thereof in any ratio;

or any of its physiologically acceptable salts.

4. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;

R(2a), R(2b) and R(2c) are hydrogen;

R(3) is hydrogen or alkyl having 1, 2, 3 or 4 carbon atoms;

Z is sulfur;

A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

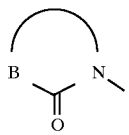

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system selected from the group consisting of the formulae:

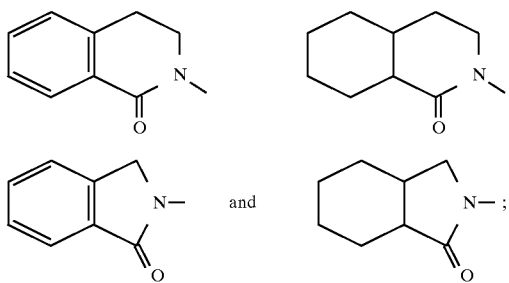

in any of its stereoisomeric forms, or a mixture thereof in any ratio;
or any of its physiologically acceptable salts.

5. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is sulfur;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

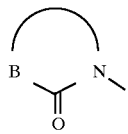

in which B is alkenylene or alkylene having 3, 4, 5 or 6 carbon atoms, which radical is unsubstituted or substituted by up to three identical or different alkyl groups having 1, 2, 3 or 4 carbon atoms;

in any of its stereoisomeric forms, or a mixture thereof in any ratio;
or any of its physiologically acceptable salts.

6. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is sulfur;
A is phenyl which is unsubstituted or substituted by up to three identical or different substituents selected from the group consisting of halogen, alkyl having 1 or 2 carbon atoms and alkoxy having 1 or 2 carbon atoms;

in any of its stereoisomeric forms, or a mixture thereof in any ratio;
or any of its physiologically acceptable salts.

7. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen or alkyl having 1, 2, 3 or 4 carbon atoms;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

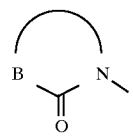

in which B is alkenylene or alkylene having 3, 4, 5 or 6 carbon atoms, which radical is unsubstituted or substituted by up to three identical or different alkyl groups having 1, 2, 3 or 4 carbon atoms, or A is the radical of a bicyclic system selected from the group consisting of the formulae:

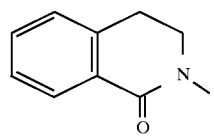 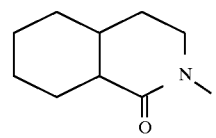

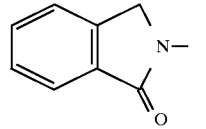 and 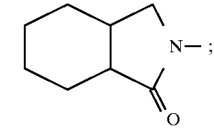 ;

in any of its stereoisomeric forms, or a mixture thereof in any ratio;
or any of its physiologically acceptable salts.

8. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms, or A is the radical of a saturated or unsaturated lactam of the formula

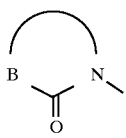

in which B is alkenylene or alkylene having 3, 4, 5 or 6 carbon atoms, which radical is unsubstituted or substituted by up to three identical or different alkyl groups having 1, 2, 3 or 4 carbon atoms;

in any of its stereoisomeric forms, or a mixture thereof in any ratio;

or any of its physiologically acceptable salts.

9. A compound of the formula (I) as claimed in claim 1, in which:

R(1) is hydrogen, alkyl having 1 or 2 carbon atoms, alkoxy having 1 or 2 carbon atoms or alkylmercapto having 1 or 2 carbon atoms;
R(2a), R(2b) and R(2c) are hydrogen;
R(3) is hydrogen, methyl or ethyl;
Z is oxygen;
A is phenyl which is unsubstituted or substituted by up to three identical or different substituents selected from the group consisting of halogen, alkyl having 1 or 2 carbon atoms and alkoxy having 1 or 2 carbon atoms;

in any of its stereoisomeric forms, or a mixture thereof in any ratio;

or any of its physiologically acceptable salts.

10. A process for the preparation of a compound of the formula (I) as claimed in claim 1, which comprises reacting a chromanylsulfonamide of the formula (III)

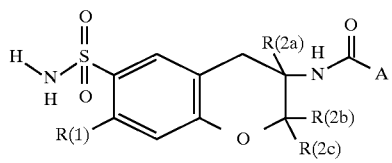

or a salt thereof of the formula (IV)

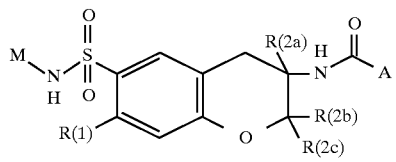

in which each of the radicals has the same meaning as recited in claim 1 and the cation M is an alkali metal or alkaline earth metal ion or an ammonium ion, with an R(3)-substituted isocyanate, an R(3)-substituted isothiocyanate, or an R(3)-substituted carbonic acid derivative.

11. A process for the preparation of a compound of the formula (I) as claimed in claim 1 in which Z is oxygen, which comprises reacting a compound of the formula (III)

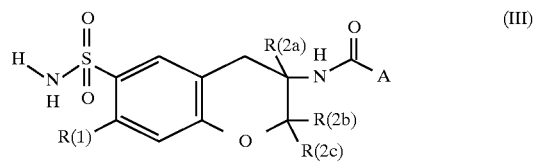

or a salt thereof of the formula (IV)

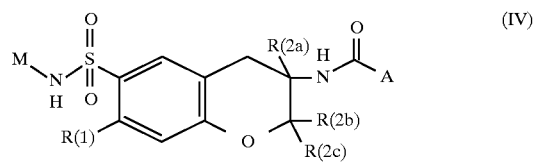

in which each of the radicals has the same meaning as recited in claim 1 and the cation M is an alkali metal or alkaline earth metal ion or an ammonium ion, with a trichloroacetamide substituted by R(3) on the nitrogen.

12. A process for the preparation of a compound of the formula (I) as claimed in claim 1 in which R(3) is hydrogen, which comprises reacting a compound of the formula (III)

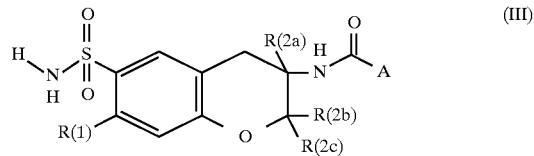

or a salt thereof of the formula (IV)

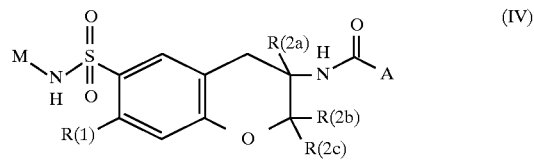

in which each of the radicals has the same meaning as recited in claim 1 and the cation M is an alkali metal or alkaline earth metal ion or an ammonium ion, with a trialkylsilyl iso(thio)cyanate or silicon tetraiso(thio)cyanate, and cleaving the primary silicon-substituted chromanylsulfonyl(thio)urea.

13. A process for the preparation of a compound of the formula (I) as claimed in claim 1 in which Z is oxygen, which comprises reacting a compound of the formula (VIII)

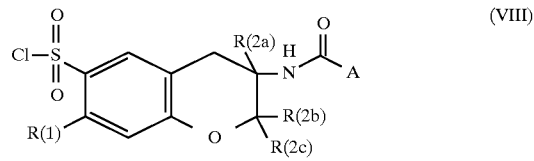

in which each of the radicals has the same meaning as recited in claim 1, with an R(3)-substituted urea or an R(3)-substituted bis(trialkylsilyl)urea.

14. A process for the preparation of a compound of the formula (I) as claimed in claim 1, which comprises reacting a compound of the formula (IX) or (X)

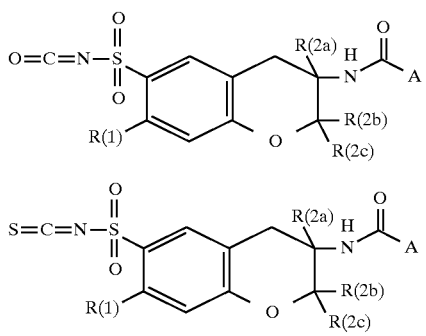

in which each of the radicals has the same meaning as recited in claim 1, with an amine of the formula R(3)-NH$_2$ in which R(3) has the same meaning as recited in claim 1.

15. A process for the preparation of a compound of the formula (I) as claimed in claim 1 in which Z is oxygen, which comprises desulfurizing a compound of the formula (I) in which Z is sulfur.

16. A pharmaceutical composition comprising a pharmaceutically effective amount of a compound of the formula (I) or a physiologically acceptable salt thereof as claimed in claim 1 together with a pharmaceutically acceptable carrier.

17. A pharmaceutical composition for treating or preventing disturbances of the cardiovascular system, cerebral vascular diseases, ischemic states of the heart, a weakened cardiac power, or for improving cardiac function after heart transplants, said composition comprising an effective amount of a compound of formula (I) or a physiologically acceptable salt thereof as claimed in claim 1 together with a pharmaceutically acceptable carrier.

18. A pharmaceutical composition for treating or preventing disturbances in cardiac rhythm or for preventing sudden cardiac death, said composition comprising an effective amount of a compound of formula (I) or a physiologically acceptable salt thereof as claimed in claim 1 together with a pharmaceutically acceptable carrier.

19. A method for treating or preventing disturbances of the cardiovascular system, cerebral vascular diseases, ischemic states of the heart, a weakened cardiac power, or for improving cardiac function after heart transplants, which comprises administering to a host in need of said treatment, prevention or improvement an effective amount of a compound of formula (I) or a physiologically acceptable salt thereof as claimed in claim 1.

20. A method for treating or preventing disturbances in cardiac rhythm or for preventing sudden cardiac death, which comprises administering to a host in need of said treatment or prevention an effective amount of a compound of formula (I) or a physiologically acceptable salt thereof as claimed in claim 1.

21. A method for inhibiting ATP-sensitive potassium channels, which comprises administering to a host in need of said inhibition, an effective amount of a compound of formula (I) or a physiologically acceptable salt thereof as claimed in claim 1.

22. A method for inhibiting ATP-sensitive potassium channels, which comprises applying to a biological sample an effective amount of a compound of formula (I) or a physiologically acceptable salt thereof as claimed in claim 1.

* * * * *

UNITED STATES PATENT AND TRADEMARK OFFICE
CERTIFICATE OF CORRECTION

PATENT NO. : 5,849,755
DATED : December 15, 1998
INVENTOR(S) : Heinrich Christian ENGLERT, et al.

It is certified that error appears in the above-indentified patent and that said Letters Patent is hereby corrected as shown below:

Title Page, Item [75], in the Iventors, line 4, "Frankurt" should read --Frankfurt--.

Claim 2, column 43, line 14, "radial" should read --radical--.

Signed and Sealed this

Sixteenth Day of November, 1999

Attest:

Q. TODD DICKINSON

*Attesting Officer*    *Acting Commissioner of Patents and Trademarks*